(12) United States Patent
Gulati

(10) Patent No.: US 6,963,806 B2
(45) Date of Patent: *Nov. 8, 2005

(54) TECHNIQUE FOR ANALYZING ARRAYED SIGNALS USING QUANTUM EXPRESSOR FUNCTIONS

(75) Inventor: Sandeep Gulati, La Canada, CA (US)

(73) Assignee: ViaLogy Corp., Altadena, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 10/639,608

(22) Filed: Aug. 12, 2003

(65) Prior Publication Data

US 2004/0064261 A1 Apr. 1, 2004

Related U.S. Application Data

(63) Continuation of application No. 09/913,132, filed as application No. PCT/US00/04076 on Feb. 17, 2000, now Pat. No. 6,671,625, which is a continuation of application No. 09/253,789, filed on Feb. 22, 1999, now Pat. No. 6,136,541.

(51) Int. Cl.[7] .................. G01N 33/48; G01N 33/50
(52) U.S. Cl. ................ 702/20; 702/19; 702/27; 435/6; 435/7.1
(58) Field of Search ............... 702/19, 20, 27; 435/6, 7.1; 703/11

(56) References Cited

U.S. PATENT DOCUMENTS

| | | | | | |
|---|---|---|---|---|---|
| 4,686,695 | A | * | 8/1987 | Macovski | 378/146 |
| 5,236,826 | A | * | 8/1993 | Marshall | 435/7.92 |
| 5,784,162 | A | | 7/1998 | Cabib et al. | |
| 6,136,541 | A | | 10/2000 | Gulati | |
| 6,142,681 | A | | 11/2000 | Gulati | |
| 6,671,625 | B1 | * | 12/2003 | Gulati | 702/20 |

\* cited by examiner

*Primary Examiner*—Mark K. Zeman
(74) *Attorney, Agent, or Firm*—Fish & Richardson P.C.

(57) ABSTRACT

A technique for determining events of interest within an output pattern generated from a detected image of an array of detectors where the output pattern comprises signals associated with noise, and signals associated with the events of interest which have intensities both greater and less than intensities of signals associated with noise. Quantum resonance interferometry is utilized to amplify signals associated with the events of interest having an intensity lower than the intensity of signals associated with noise, to an intensity greater than the intensity of the signals associated with noise to generate a modified output pattern. Once the desired signals are amplified, the technique determines which signals within the modified output pattern correlate with events of interest thus permitting a determination to be made whether a certain event of interest has occurred.

20 Claims, 6 Drawing Sheets

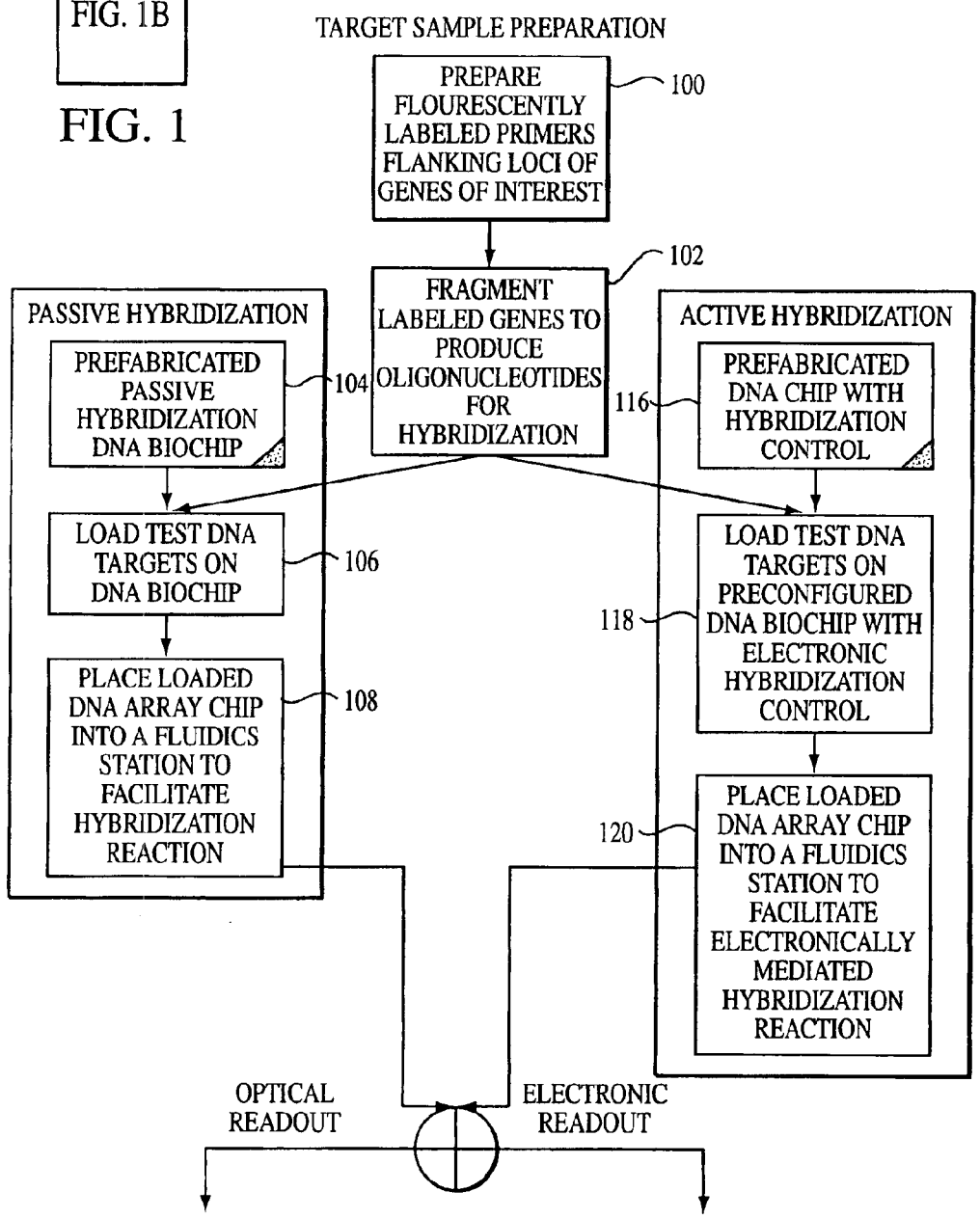

TECHNIQUE FOR ANALYZING ARRAYED SIGNALS USING QUANTUM EXPRESSOR FUNCTIONS

CLAIM OF PRIORITY

This application is a continuation of U.S. patent application Ser. No. 09/913,132, filed Aug. 9, 2001, now U.S. Pat. No. 6,671,625, which is a national stage application of PCT US00/04076 filed on Feb. 17, 2000, which is a continuation of and claims priority to U.S. patent application Ser. No. 09/253,789, filed on Feb. 22, 1999 now U.S. Pat. No. 6,136,541.

FIELD OF THE INVENTION

The invention generally relates to techniques for analyzing biological samples such as DNA, RNA, or protein samples and in particular to techniques for analyzing the output patterns of hybridized biochip microarrays.

BACKGROUND OF THE INVENTION

A variety of techniques have been developed to analyze DNA or other biological samples to identify diseases, mutations, or other conditions present within a patient providing the sample. Such techniques may determine, for example, whether the patient has any particular disease such as cancer or AIDS, or has a predisposition toward the disease, or other medical conditions present in the patient.DNA-based analysis may be used either as an in-vitro or as an in-vivo control mechanism to monitor progression of disease, assess effectiveness of therapy or be used to design dosage formulations. DNA-based analysis is used verify the presence or absence of expressed genes and polymorphisms.

One particularly promising technique for analyzing biological samples uses a DNA-based microarray (or microelectronics biochip) which generates a hybridization pattern representative of the characteristics of the DNA within the sample. Briefly, a DNA microarray includes a rectangular array of immobilized single stranded DNA fragments. Each element within the array includes few tens to millions of copies of identical single stranded strips of DNA containing specific sequences of nucleotide bases. Identical or different fragments of DNA may be provided at each different element of the array. In other words, location (1,1) contains a different single stranded fragment of DNA than location (1,2) which also differs from location (1,3) etc. Certain biochip designs may replicate the nucleotide sequence in multiple cells.

DNA-based microarrays deploy chemiluminiscence, fluorescence or electrical phenomenology to achieve the analysis. In methods that exploit fluorescence imaging, a target DNA sample to be analyzed is first separated into individual single stranded sequences and fragmented. Each sequence being tagged with a fluorescent marker molecule. The fragments are applied to the microarray where each fragment binds only with complementary DNA fragments already embedded on the microarray. Fragments which do not match any of the elements of the microarray simply do not bind at any of the sites of the microarray and are discarded during subsequent fluidic reactions. Thus, only those microarray locations containing fragments that bind complementary sequences within the target DNA sample will receive the fluorescent molecules. Typically, a fluorescent light source is then applied to the microarray to generate a fluorescent image identifying which elements of the microarray bind to the patient DNA sample and which do not. The image is then analyzed to determine which specific DNA fragments were contained within the original sample and to determine therefrom whether particular diseases, mutations or other conditions are present in the patient sample.

For example, a particular element of the microarray may be exposed to fragments of DNA representative of a particular type of cancer. If that element of the array fluoresces under fluorescent illumination, then the DNA of the sample contains the DNA sequence representative of that particular type of cancer. Hence, a conclusion can be drawn that the patient providing the sample either already has that particular type of cancer or is perhaps predisposed towards that cancer. As can be appreciated, by providing a wide variety of known DNA fragments on the microarray, the resulting fluorescent image can be analyzed to identify a wide range of conditions.

Unfortunately, under conventional techniques, the step of analyzing the fluorescent pattern to determine the nature of any conditions characterized by the DNA is expensive, time consuming, and somewhat unreliable for all but a few particular conditions or diseases. One major problem with many conventional techniques is that the techniques have poor repeatability. Hence, if the same sample is analyzed twice using two different chips, different results are often obtained. Also, the results may vary from lab to lab. Consistent results are achieved only when the target sample has high concentrations of oligonucleotides of interest. Also, skilled technicians are required to prepare DNA samples, implement the hybridization protocol, and analyze the DNA microarray output possibly resulting in high costs. One reason that repeatability is poor is that the signatures within the digitized hybridization pattern (also known as a "dot spectrogram") that are representative of mutations of interest are typically very weak and are immersed in considerable noise. Conventional techniques are not particularly effective in extracting mutation signatures from dot spectrograms in low signal to noise circumstances. Circumstances wherein the signal to noise ratio is 0 to strongly negative (−2 to −30 dB) are particularly intractable.

Accordingly, it would highly desirable to provide an improved method and apparatus for analyzing the output of the DNA microarray to more expediently, reliably, and inexpensively determine the presence of any medical conditions or concerns within the patient providing the DNA sample. It is particularly desirable to provide a technique that can identify mutation signatures within dot spectrograms even in circumstance wherein the signal to noise ration is extremely low. It is to these ends that aspects of the invention are generally drawn.

Referring now to FIG. 1, conventional techniques for designing DNA microarray chips and for analyzing the output thereof will now be described in greater detail. Initially, at step 100, fluorescently labeled primers are prepared for flanking loci of genes of interest within the DNA sample. The primers are applied to the DNA sample such that the fluorescently labeled primers flank genes of interest. At step 102, the DNA sample is fragmented at the locations where the fluorescently labeled primers are attached to the genes of interest to thereby produce a set of DNA fragments, also called "oligonucleotides" for applying to the DNA microarray.

In general, there are two types of DNA microarrays: passive hybridization microarrays and active hybridization microarrays. Under passive hybridization, oligonucleotides characterizing the DNA sample are simply applied to the DNA microarray where they passively attach to complementary DNA fragments embedded on the array. With active hybridization, the DNA array is configured to externally enhance the interaction between the fragments of the DNA samples and the fragments embedded on the microarray using, for example, electronic techniques. Within FIG. 1, both passive hybridization and active hybridization steps are illustrated in parallel. It should be understood that, currently for any particular microarray, either the passive hybridization or the active hybridization steps, but not both, are typically employed. Referring first to passive hybridization, at step 104 a DNA microarray chip is prefabricated with oligonucleotides of interest embedded or otherwise attached to particular elements within the microarray. At step 106, the oligonucleotides of the DNA sample generated at step 102 are applied to the microarray. Oligonucleotides within the sample that match any of the oligonucleotides embedded on the microarray passively bind with the oligonucleotides of the array while retaining their fluorescently labeled primers such that only those locations in the microarray having corresponding oligonucleotides within the sample receive the primers. It should be noted that each individual nucleotide base within the oligonucleotide sequence (with lengths ranging from 5 to 25 base pairs) can bond with up to four different nucleotides within the microarray, but only one oligonucleotide represents an exact match. When illuminated with fluorescent light, the exact matches fluoresces most effectively and the non-exact matches fluoresce considerably less or not at all.

At step 108, the DNA microarray with the sample loaded thereon is placed within a fluidics station provided with chemicals to facilitate the hybridization reaction, i.e., the chemicals facilitate the bonding of the oligonucleotide sample with corresponding oligonucleotides within the microarray. At step 110, the microarray is illuminated under fluorescent light, perhaps generated using an ion-argon laser, and the resulting fluorescent pattern is digitized and recorded. Alternately, a photograph of the fluorescent pattern may be taken, developed, then scanned into a computer to provide a digital representation of the fluorescent pattern. In any case, at step 112, the digitized pattern is processed using dedicated software programs which operate to focus the digital pattern and to subsequently quantize the pattern to yield a fluorescent intensity value for each array within the microarray pattern. At step 114, the resulting focused array pattern is processed using additional software programs which compute an average intensity value at each array location and provides for necessary normalization, color compensation and scaling. Hence, following step 114, a digitized fluorescent pattern has been produced identifying locations within the microarray wherein oligonucleotides from the DNA sample have bonded. This fluorescent pattern is referred to herein as a "dot spectrogram".

In existing biochips that actively initiate, facilitate or selectively block hybridization, a DNA microarray is prefabricated for active hybridization at step 116. At step 118, the DNA sample is applied to the active array and electronic signals are transmitted into the array to help facilitate bonding between the oligonucleotides of the sample and the oligonucleotides of the array. The microarray is then placed within a fluidics station which further facilitates the bonding. Thereafter, at step 122, an electronic or fluorescent readout is generated from the microarray. When electrical output signals from the biochip array are used to quantify and classify the post-hybridization output, the output signal is indicative of the number oligonucleotide fragments bonded to each site within the array. At step 124 the electronic output is processed to generate a dot spectrogram similar or identical to the dot spectrogram generated using the optical readout technique of steps 110–114. Hence, regardless of whether steps 104–114 are performed or steps 116–124 are performed the result is a dot spectrogram representative of oligonucleotides present within the DNA sample. Here it should be noted that some conventional passive hybridization DNA microarrays provide electronic output and some active hybridization microelectronic arrays provide optical readout. Thus, for at least some techniques, the output of step 108 is processed in accordance with steps 122 and 124. For other techniques, the output of step 120 is processed in accordance with steps 110–114. Again, the final results are substantially the same, i.e., a dot spectrogram.

At step 126, the dot spectrogram is analyzed using clustering software to generate a gene array amplitude readout pattern representative of mutations of interest within the target DNA sample. In essence, step 126 operates to correlate oligonucleotides represented by the dot spectrogram with corresponding DNA mutations. Next, at step 128, the resulting digital representation of the mutations of interest are processed using mapping software to determine whether the mutations are representative of particular diagnostic conditions, such as certain diseases or conditions. Hence, step 128 operates to perform a mutation-to-diagnostic analyses. Finally, at step 130 the diagnostic conditions detected using step 128 are evaluated to further determine whether or not the diagnostic, if any, can properly be based upon the DNA sample. Classical methods such as probabilistic estimator such as minimum a posteriori (MAP) estimator, maximum likelihood estimator (MLE) or inferencing mechanism may be used to render a diagnostic assessment.

As noted above, it would be desirable to provide improved techniques for analyzing the outputs for DNA microarrays to more quickly, reliably and inexpensively yield a valid diagnostic assessment. To this end, the invention is directed primarily to providing a sequence of steps for replacing steps 114–130 of FIG. 1.

SUMMARY OF THE INVENTION

In accordance with a first aspect of the invention, a method is provided for analyzing an output pattern of a biochip to identify mutations, if any, present in a biological sample applied to the biochip. In accordance with the method, a resonance pattern is generated which is representative of resonances between a stimulus pattern associated with a set of known mutations and the output pattern of the biochip. The resonance pattern is interpreted to yield a set of confirmed mutations by comparing resonances found therein with predetermined resonances expected for the selected set of mutations.

In an exemplary embodiment, the biological sample is a DNA sample and the output pattern being analyzed is a quantized dot spectrogram generated by a hybridized oligonucleotide microarray. The resonance pattern is generated by iteratively processing the dot spectrogram by performing a convergent reverberation to yield a resonance pattern representative of resonances between a predetermined set of selected Quantum Expressor Functions and the dot spectrogram until a predetermined degree of convergence is achieved between the resonances found in the resonance pattern and resonances expected for the set of mutations. The resonance pattern is analyzed to yield a set of confirmed mutations by mapping the confirmed mutations to known diseases or diagnostic conditions of interest, associated with the pre-selected set of known mutations to identify diseases, if any, indicated by the DNA sample. A diagnostic confirmation is then made by taking the identified diseases and solving in reverse for the associated Quantum Expressor Functions and then comparing those Quantum Expressor Functions with ones expected for the mutations associated with the identified disease to verify correspondence. If no correspondence is found, a new sub-set of known mutations are selected and the steps are repeated to determine whether any of the new set of mutations are present in the sample.

In the exemplary embodiment the set of nonlinear Quantum Expressor Functions are generated are follows. A set of mutation signatures representative of the pre-selected set of known mutations is input. A representation of a microarray oligonucleotide pattern layout for the microarray, from which the dot spectrogram is generated, is also input. Then a set of resonant interaction parameters are generated which are representative of mutation pattern interactions between elements of the microarray including interactions from a group including element-to-element interactions, element-to-ensemble interactions, ensemble-to-element interactions, and ensemble-to-ensemble interactions. Then the set of nonlinear Quantum Expressor Functions are generated from the set of resonant interaction patterns by matching selected harmonics of the power spectral density (PSD) amplitude of a coded mutation signature, corresponding to the pre-selected mutation set of interest, to that of a pre-determined quantum-mechanical Hamiltonian system so that stochastic and deterministic time scales match, and the time scales couple back to noise statistics and degree of asymmetry.

Also in the exemplary embodiment, the dot spectrogram is differentially enhanced prior to the generation of the resonance pattern by refocusing the dot spectrogram to yield a re-focused dot spectrogram; cross-correlating the re-focused dot spectrogram; applying a local maxima filter to the correlated re-focused dot spectrogram to yield a maximized dot spectrogram; re-scaling the maximized dot spectrogram to yield a uniformly re-scaled dot spectrogram; and then re-scaling the uniformly re-scaled dot spectrogram to amplifying local boundaries therein to yield a globally re-scaled dot spectrogram.

By exploiting a resonant interaction, mutation signatures may be identified within a dot spectrogram even in circumstances involving low signal to noise ratios or, in some cases, negative signal to noise ratios. By permitting the mutation signatures to be identified in such circumstances, the reliability of dot spectrogram analysis is thereby greatly enhanced. With an increase in reliability, costs associated with performing the analysis are decreased, in part, because there is less of a requirement for skilled technicians. Other advantages of the invention arise as well.

In accordance with a second aspect of the invention, a method of generating a set of nonlinear Quantum Expressor Functions is provided. The method includes the steps of inputting a set of mutation signatures representative of the pre-selected set of known mutations and inputting a representation of a biochip layout. The method also includes the steps of generating a set of resonant interaction parameters representative of mutation pattern interactions between elements of the microarray including interactions from a group including element-to-element interactions, element-to-ensemble interactions, ensemble-to-element interactions, and ensemble-to-ensemble interactions and generating the set of nonlinear Quantum Expressor Functions from the set of resonant interaction patterns.

Among other applications, principles of the invention are applicable to the analysis of various arrayed biomolecular, ionic, bioelectronic, biochemical, optoelectronic, radio frequency (RF) and electronic microdevices. Principles of the invention are particularly applicable to mutation expression analysis at ultra-low concentrations using ultra-high density passive and/or active hybridization DNA-based microarrays. Techniques implemented in accordance with the invention are generally independent of the physical method employed to accumulate initial amplitude information from the bio-chip array, such as fluorescence labeling, charge clustering, phase shift integration and tracer imaging. Also, principles of the invention are applicable to optical, optoelectronic, and electronic readout of hybridization amplitude patterns. Furthermore, principles of the invention are applicable to molecular expression analysis at all levels of abstraction: namely DNA expression analysis, RNA expression analysis, protein interactions and protein—DNA interactions for medical diagnosis at the molecular level.

Apparatus embodiments are also provided.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein.

DETAILED DESCRIPTION OF EXEMPLARY EMBODIMENTS

Figure 1B:
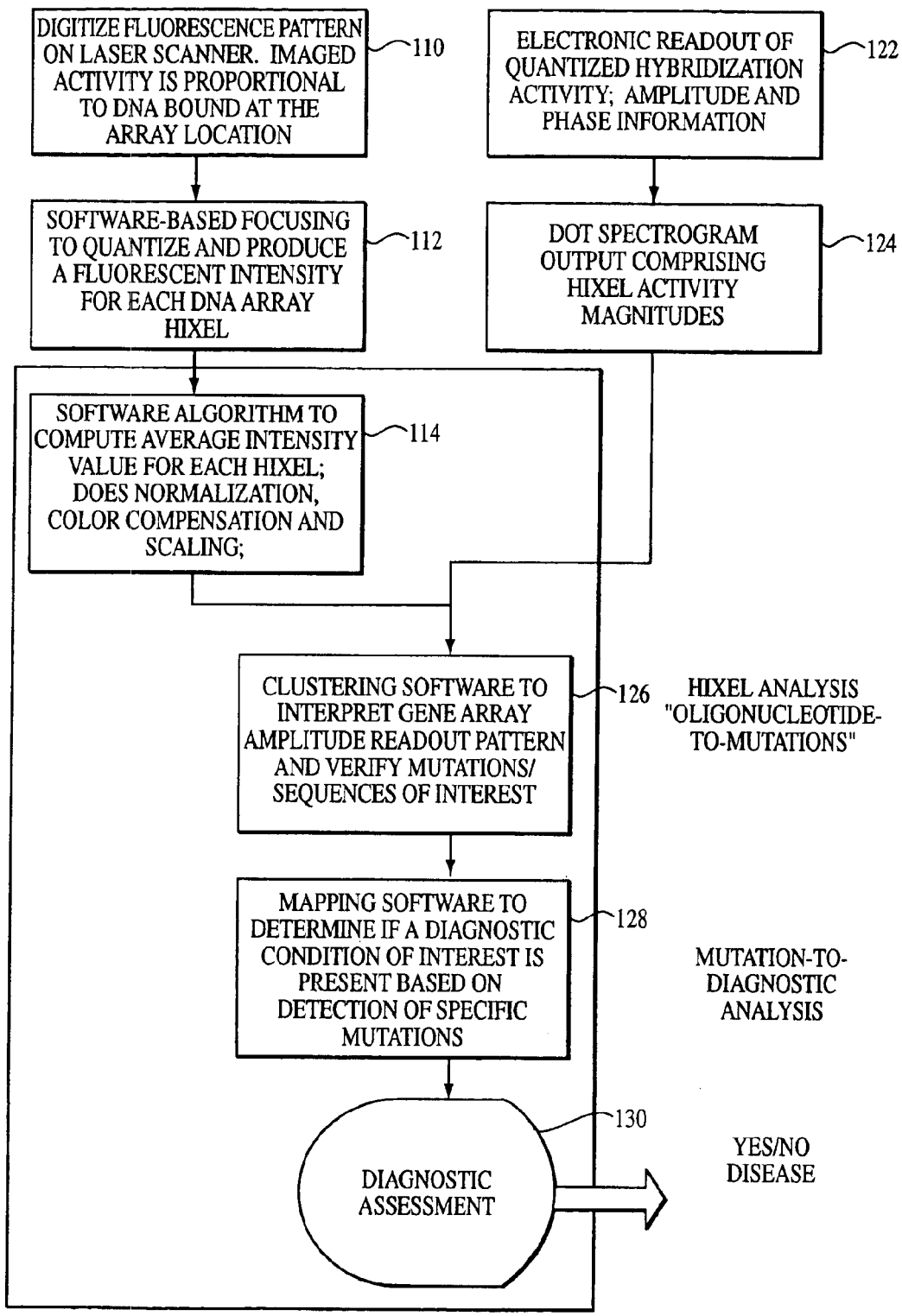
FIG. 1 is a flow chart illustrating conventional passive and active hybridization DNA microarray analysis techniques.

With reference to the remaining figures, exemplary embodiments of the invention will now be described. The invention will be described primarily with respect to an exemplary method for analyzing mutations signatures within output patterns of hybridized microarrays generated using DNA samples, but principles of the invention apply to the analysis of other protein-based samples or to other types of output patterns as well.

Overview

Briefly, the exemplary method exploits, among other features: (a) a novel representation, interpretation and mathematical model for the immobilized oligonucleotide hybridization patterns, represented via a dot spectrogram; (b) a new "active" biomolecular target detection and discrimination method based on quantum resonance interferometry, and (c) a new spatial hashing function that yields accurate diagnostic assessment.

To this end, the exemplary method exploits a fundamentally different computational paradigm for mutation expression detection in pre-enhanced dot spectrogram realizations. The method is an innovative modification to dynamically arrayed quantum stochastic resonance (QSR) for discrete system analysis. The arraying strategy is a function of the expression pathway of interest. The method depends on the molecular diagnostic spectrum being addressed. Coupled quantum resonators are employed to significantly enhance signal-to-noise (SNR) performance and fuse multiple synthetic renormalized dot spectrogram realizations to better detect prespecified biomolecular expression patterns.

Moreover the exemplary method exploits an enhancement in previous extensions to classical stochastic resonance (SR) and array enhanced SR (AESR) in signal processing and sensor data analysis. Stochastic resonance is a phenomenon wherein the response to a sensor, modeled in terms of a bistable nonlinear dynamical system, is enhanced by applying a random noise element and a periodic sinusoidal forcing function. SR occurs when the SNR passes through a maximum as the noise level is increased.

Thus an important aspect of the exemplary method involves the coupling of transformed and preconditioned discrete microarray outputs to a mathematical model for a quantum-mechanical dynamical system with specific properties. When driven in a particular manner, the coupled system exhibits a nonlinear response that corresponds to detection of phenomena of interest. The method exploits modulation of observables from a "base" (canonical continuous dynamical system), so that a selected set of spectral properties match a similar selected spectral properties of a discrete spatial tessellation substructure from an amplitude spectrogram derived from bioelectronic observables. The method further exploits the concept of convolving a discrete spatial system (derived from base mutants of interest) with a continuous asymmetric temporal system to derive a spatiotemporal input to further convolve with another discrete spatial projection (of an inherently partially stabilized spatiotemporal system).

Hence key components of the exemplary biomolecular detection method are: (i) selection of a basis system; (ii) generation of designer Quantum Expressor Function (QEF) for coupling with the substrate to be analyzed; (iii) generation of a Hamiltonian to describe relaxation dynamics of the coupled system; (iv) modulation of resonance parameters to enforce early resonance; (v) and exploitation of resonance suppressors to verify detection.

The Method

Figure 2:
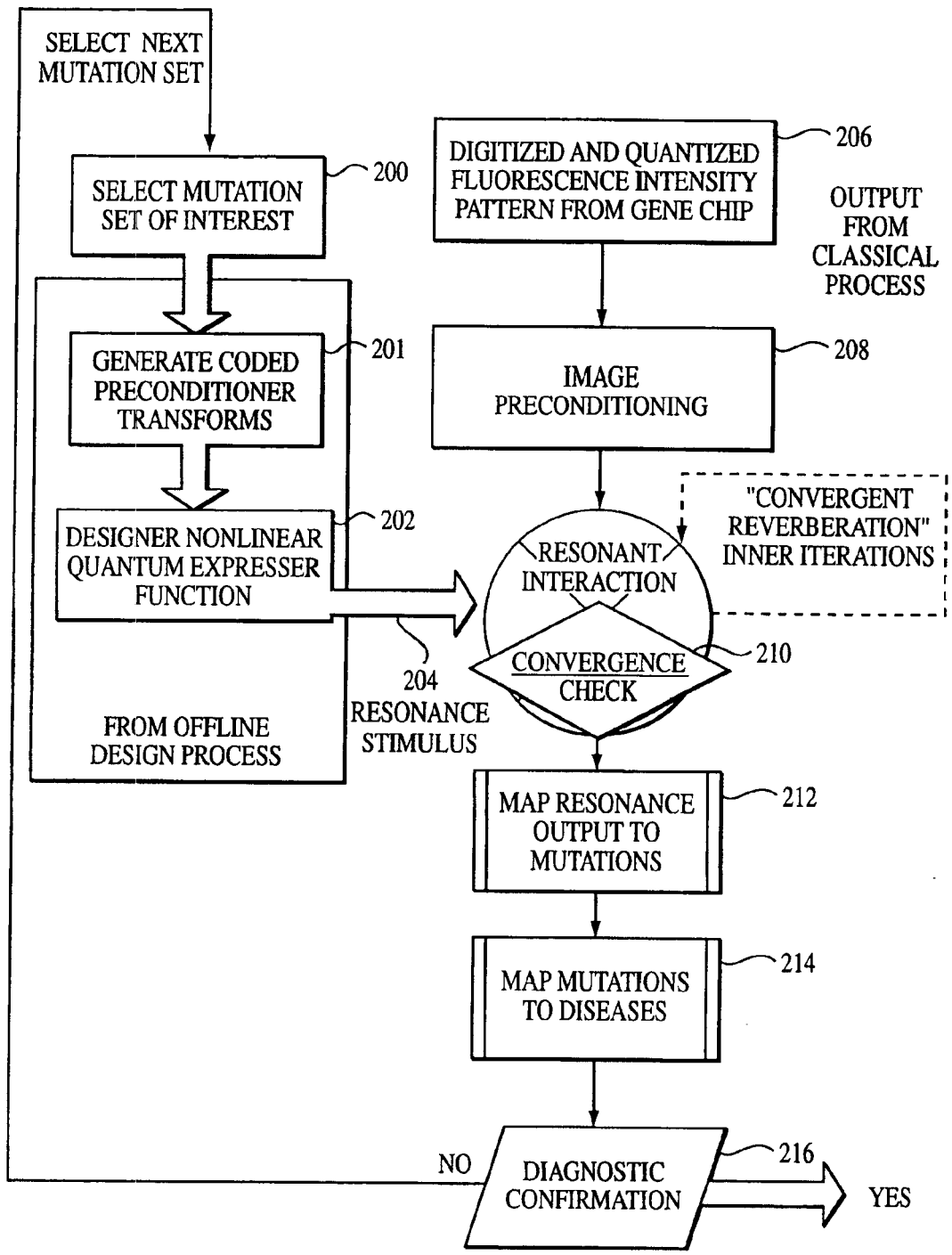
FIG. 2 is a flow chart illustrating an exemplary method for analyzing the output of a hybridized DNA microarray in accordance with the invention.

Referring first to FIG. 2, initially at step 200, a set of mutations of interest is selected. The mutations, for example, may be mutations relevant to cancer, AIDS, or other diseases or medical conditions. At step 201, preconditioner transforms are generated based upon the selected set of mutations. The preconditioner transforms are provided to convert mutation nucleotide sequences into expected amplitude patterns in the prespecified microarray representation, given a particular biochip layout. At step 202, Quantum Expressor Functions are generated based upon the Hamiltonian of a pre-selected basis system. The Quantum Expressor Functions are designed to couple the Hamiltonian for the selected basis system to a predetermined DNA microarray configuration to permit a resonance interaction involving the output of the DNA microarray. Resonance stimulus is generated, at step 204, using the Quantum Expressor functions.

What has been summarized thus far are preliminary steps performed off-line for setting up the Quantum Expressor Functions and the corresponding resonance stimulus. These steps need be performed only once for a given set of mutations and for a given DNA microarray configuration. Thereafter, any number of output patterns from the DNA microarray may be processed using the Quantum Expressor Functions to identify whether any of the mutations of the pre-selected set of mutations are found therein. Preferably, Quantum Expressor Functions are pre-generated for a large set of mutations and for a large set of DNA microarray patterns such that, for each new DNA microarray output pattern from each new patient sample, the presence of any of the mutations can be quickly identified using the predetermined set of Quantum Expressor Functions. In general, the aforementioned steps need be repeated only to update the Quantum Expressor Functions to accommodate new and different DNA microarray patterns or to if new mutations of interest need to be considered.

At step 206, an output pattern (referred to herein as a Dot Spectrogram) is generated using a DNA microarray for which Quantum Expressor Functions have already been generated. At step 208, the dot spectrogram is preconditioned to yield a dot spectrogram tesselation (DST) to permit exploitation of a resonance interaction between the dot spectrogram and the Quantum Expressor Functions. The actual resonant interaction, which involves convergent reverberations, is performed at step 210 until a predetermined degree of convergence is achieved. Once convergence is achieved, a resulting resonance pattern is processed at step 212 to identify any mutations represented thereby. As will be described below, step 212 is rendered trivial by virtue of the aforementioned resonant interaction which is based upon Quantum Expressor Function already correlated with the pre-selected mutations. Hence, no complicated analysis is required to interpret the resonance pattern to identify the mutations. Next, at step 214, the mutations are mapped to corresponding diseases and conditions to thereby identify any diseases or conditions that the patient providing the sample being analyzed is afflicted with. Again, this is a fairly trivial step. Finally, at step 216, diagnostic confirmation is preformed to verify that the diseases or conditions are present in the sample. This is achieved by starting with the found diseases or conditions and then performing the steps of the method in reverse.

Figure 3:
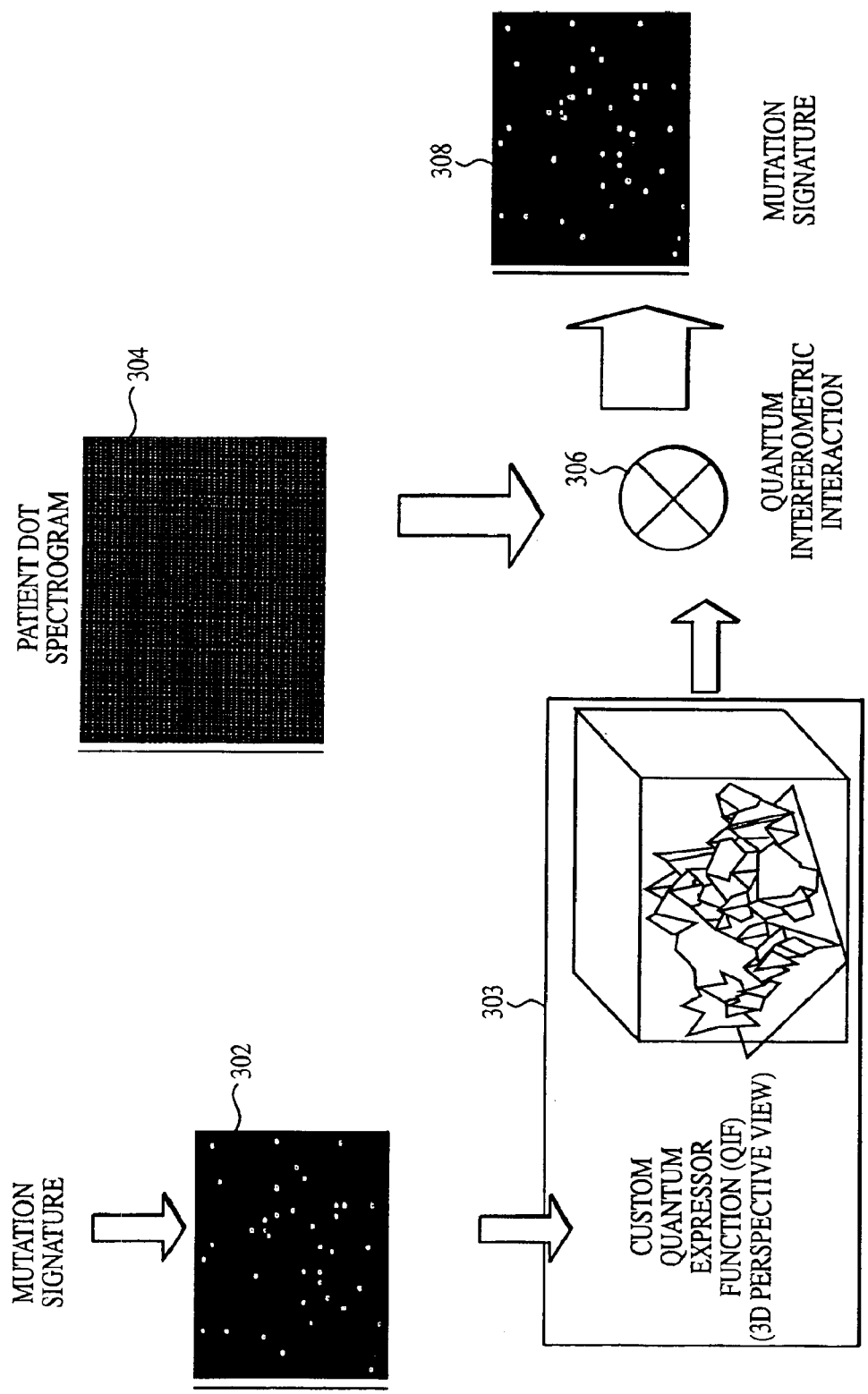
FIG. 3 graphically illustrates the method of FIG. 2.

FIG. 3 graphically illustrates the operation of the method of FIG. 2 whereby a Quantum Expressor Function 300 is generated based on a mutation set 302. A dot spectrogram 304 is applied to the Quantum Expressor Function via an interferometric resonance interaction 306 yielding a resonance pattern (not shown) from which mutations signatures 308 (representative of mutations present in the sample from which the dot spectrogram was generated) may be identified by comparison with mutation set 302.

Now details of the various steps of the method will be provided.

Mutations Sets

Referring again to FIG. 2, the mutation set of interest generated at step 200 is selected by identifying oligonucleotides representative of the $\{Z\}$ mutations of interest. Each oligonucleotide is represented by $\psi(i,j)$ which is given by $[\alpha_0 \alpha_1 \ldots \alpha_k]$, where $\alpha=\{A,C,T,G\}$ base associated with each array cell [a,b] where $10 \leq k \leq 25$. The entire set of unique oligonucleotides denoting mutations of interest, $\Delta(l,m)$, is given by $[\delta_0 \delta_1 \ldots \delta_k]$ where $\delta=\{A,C,T,G\}$ length $|\Delta|=$length $|\psi|$, and $0<\|\Delta-\psi\| \leq k$, and the designed in $\psi(l,m)$ oligonucleotide sequence is a perfect complement to only $\Delta(l,m)$ for all l,m.

As part of step 200, an oligonucleotide table is generated which contains the oligonucleotide sequences associated with each mutation of interest identified by row and column location (i,j). The oligonucleotide table is provided for subsequent use at step 212 to map locations within the dot spectrogram wherein resonance occurs at step 210 to oligonucleotides such that mutations present in a sample being analyzed are easily identified. Also as part of step 200, a mutation table is generated which contains the diseases associated with each mutation of interest. The mutation table is provided for subsequent use at step 214 to map mutations identified at step 212 to specific diseases or other medical conditions such that the diseases can be easily identified.

Preconditioner Transforms

Given the microarray layout and the mutations of interest (in the coordinate system specified by the prespecified exemplary microarray layout) preconditioner transforms are employed at step 201 to generate an amplitude pattern and associated point spread function at a signal-to-noise ratio (SNR)=0.

In the exemplary embodiment, the DNA microarray is an N by M DNA chip array wherein an element of the array is referred to herein as an "oxel": o(i,j).

The pre-hybridization microarray (PEBC) is expressed as:

$$PEBC = \sum_{1}^{N}\sum_{1}^{M} o(i, j),$$

where N and M refer to the linear (row and column) dimensions of the 2-D microarray.

An inverse Dirichlet Tessellation (IDT) on the PEBC is applied such that a singular value decomposition (SVD) on the resulting array yields the location of the mutation of interest at the SNR=0 condition. Conceptually the process corresponds to setting up a concave diffusion front at the mutation-centered oxel.

The equations used are $x_f = k_x(Dt)^{1/2}$ $\sigma_f = k_\sigma(Dt)^{\alpha\sigma/2}$ where $\alpha_{94} = 4/7$.

$N_f = k_N L(Dt)^{\alpha N/2}$ where $\alpha_N = 3/7$.

$D_H = 7/4$.

The constants $k_x$, $k\sigma$ and $k_N$ are respectively set to 0.856, 0.68, and 1.34, and for biochip dimensions N,M>100, t is typically set to $10^2 * a^2/D$ where a=inter-oxel distance and D is a coefficient for percolation of the point spread. D is chosen as 0.001. These equations impose a specific IDT, i.e., rapid diffusion on the mutation-centered oxel, and synthetically tessellate the biochip.

Basis System for Quantum Expressor Functions

To generate Quantum Expressor Functions (QEF) at step 202, a basis system for the QEF is first selected. The selection of the basis system and the generation of the QEF's based thereon depends, in part, and the characteristics of the DNA microarray.

The numeric value associated with each oxel is given by:

$\hat{O}(i,j) = \alpha_k \cdot 4^{k-1} + \alpha_{k-1} \cdot 4^{k-2} + \ldots + \alpha_1 \cdot 4^1 + \alpha_0 \cdot 4^0$ where [α]=[A|C|T|G] take the values [0|1|2|3] respectively.

An element of the dot spectrogram is referred to herein as a hixel: h(i,j).

The complete spatial randomness (CSR) hypothesis for the dot spectrogram spatial point pattern is violated by the microarray oxel layout to maximize posteriori detectability. This means that (i) Correct Binding (CB)-intensity i.e., number of spatial events (hixels with correct bindings) do not follow a Poisson Distribution; and (ii) sampled bindings do not represent independent random sample from a uniform distribution on POBC.

Compliance to CSR hypothesis would imply constant CB-intensity over the DST, as well as no interactions (inhibitions or reinforcement) among the non-zero intensity hixels. Both imply an idealized microarray design with positive SNR performance. Thus proclivity for aggregation during hybridization is assumed. Computationally, this method assumes that a 1000×1000 microarray (i.e., N=1, 000,000 oxels) is reduced to <O(100) nodes with the preconditioning method presented below. DST algorithm on preconditioned hixel array, such as variants of Dirichlet tessellation would further reduce it to ~O(10) with no coding. Consequently, this method must be applied to ~O(10) ensembles. For ultra-sensitive detection, it is assumed that the ensemble basis system is degenerate, i.e., it has (i) a bounded intensity function; (ii) a bounded radial distribution function, (iii) and is anisotropic. The method is however valid if hixel intensity distribution can be approximated by lattice-based processes, Cox processes, Markov point processes as well as homogeneous and non-homogeneous Poisson processes. Accommodating the complete spatial randomness (CSR) conditions, within a tessellation, to analyze "degenerate, contagious distributions" is actually paradoxical to the lineage from QSR and violate temporal linearity and contiguity assumptions for amplification of certain spatial effects.

Figure 4:
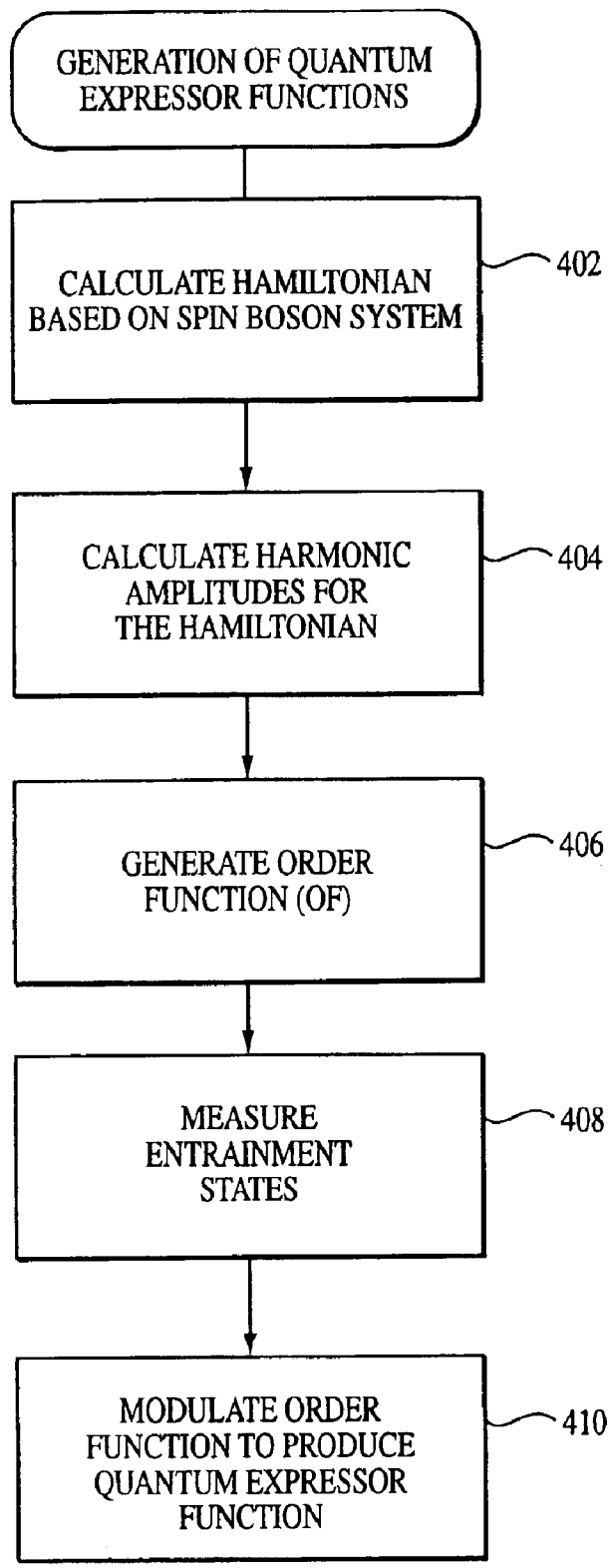
FIG. 4 is a flow chart illustrating an exemplary method for generating Quantum Expressor Functions for use with the method of FIG. 2.

Quantum Expressor Functions As noted, the Quantum Expressor Functions (QEF's) generated at step 202 are based upon the DNA chip used to generate the dot spectrogram and based upon the mutation set of interest. More specifically, as shown in FIG. 4, the QEF is generated based upon the spin Boson basis system by first calculating the Hamiltonian for the system at step 402 then, at step 404, calculating harmonic amplitudes $|P_m|$ for the Hamiltonian. Next, at step 406, an order function (OF) is generated, then at step 408, entrainment states are measured of the OF of the ground truth. Finally, at step 410, the OF of ground truth is modulated to yield the QEF.

The use of the spin-boson Hamiltonian permits the exploitation of quantum stochastic resonance (QSR) phenomena. Classical QSR is an archetypal example of a phenomenon where quantum noise is exploited to drive order in a quantum-mechanical system, as opposed to Gaussian noise in a classical system. The appearance of a resonance requires an asymmetry in the energies of the two states. A rate equation can be constructed for the system, such that the dynamics can be characterized in terms of transition rates Φ+ and Φ− between the two asymmetric quantum superposition states, and when the drive frequency and the interwell transition rates are much slower than the intrawell relaxation rates. The signal to noise ration (SNR) of such a superposition system is given by:

$$SNR = \frac{\pi}{4} \frac{\Phi_{+0}}{1+\exp[\varepsilon_0/\kappa_B T_0]} \left[\delta\left[\frac{\varepsilon}{\kappa_B T}\right]\right]^2 \varepsilon$$

Where $\kappa_B$ is the Boltzmann's constant, and T is the temperature. The sinusoidally modulated $\varepsilon = \varepsilon_0 + \delta_\varepsilon \times \cos \omega_s t$ asymmetry energy ε is given by:

$C(\tau) = \langle n_+(t+\tau|q_+,t)n_+(t|q_0,-\infty)\rangle$

In the above expression the power spectrum S(ω) represents the Fourier transform of C(τ), containing a roughly Lorentzian broadband noise background and δ-function peaks at ω=0, the driving frequency $\omega_s$, and its harmonics.

The measured correlation function for the quantum noise is given by $C(t)=<n_{+,i}(t)n_{+1}(t+\tau)>$, where each $n_{+1}=0$ or 1, and the <, indicates an average over t over many data points i taken at equal intervals, and is given by The probability of being in the + quantum state at t after being in the state $q_0$ at is given by $$n_+(t|q_0,-\infty).$$

QSR occurs for an asymmetric well, but not for a symmetric energy well.

A custom Hamiltonian, for use with step 402, which couples the above system to an ensemble of harmonic oscillators is given by $$H = \frac{1}{2}\varepsilon\sigma_z - \frac{1}{2}\hbar\Delta\sigma_x + \sigma_y\sum_\eta V_\mu(\xi_\eta + \xi_\eta^\lambda) + \hbar\sum_\eta \omega_\eta$$

The dissipative tunneling of the quantum system can be described by the above Hamiltonian. In the above expression, $\epsilon$ denotes the asymmetric energy, $\Delta$ is the tunneling matrix element, and $\sigma_i$ are the Pauli spin matrices, and $\zeta_\eta$ is a harmonic oscillator creation operator with frequencies $\omega_\eta$.

The information about the effects of the environment is contained in the spectral density $$J(\omega) = (\pi/2) \times \sum_\eta V_\eta^2 \delta(\omega - \omega_\eta).$$

However bulk of QSR results to date are limited to either experimental observations in esoteric quantum-mechanical systems (e.g., coherent motion of a wave packet in double quantum-well (DQW) semiconductor heterostructures) under specific conditions or explanations of experiments under carefully controlled conditions. It does not appear that any algorithmic implementations or methods have been designed or implemented to enforce nonlinear resonance in spatial, temporal or spatio-temporal phenomena in discrete systems by coupling such systems with another mathematical system.

Thus, as noted above, an important aspect of the exemplary method of the invention is to couple the transformed and preconditioned discrete microarray output to a mathematical model for a quantum-mechanical dynamical system with specific properties. Specific exemplary parameters for use in calculating the Hamiltonian are those proposed by A. J. Legett et al., *Reviews of Modern Physics*, 59, 1, 1987 and A. O. Caldiera and A. J. Legett *Annals of Physics*, 149, 374, 1983. The parameters are important only for an offline simulation of this spin Boson system on a digital computer. The empirical observables are then collected and used to estimate and compute spectral properties, which are actually used by the method.

It is believed that any experimentally or analytical valid parameters for the above system will work with the technique because the robustness of the method depends only on the bulk and qualitative property shown by this system and the properties of its power spectra. This is an important point since the method is actually substantially immune to nuances and specifies of the actual driving mathematical system.

The harmonic amplitudes determine the weights of $\delta$ spikes of an averaged spectral power density in an asymptotic state $S^0(\omega)$. $\epsilon$ refers to the coupling strength and $P_0$ defines the equilibrium state in the absence of driving force.

The power amplitudes $\eta_m$ in the mth frequency component of asymptotic state space are calculated at step 404 using $$\eta_m(\Omega,\epsilon) = 4\pi|P_m(\Omega,\epsilon)|$$

and the phase shift is given by $$\varphi_m(\Omega,\varepsilon) = \tan^{-1}\left[\frac{\mathrm{Im}(P_m(\Omega,\varepsilon))}{\mathrm{Re}P_m(\Omega,\varepsilon)}\right].$$

The analytic for the external force is given by $$P_m(\Omega,\varepsilon) = \frac{\gamma}{\gamma - i\mathrm{m}\Omega} \frac{2\omega_c}{\pi} h(-i\mathrm{m}\Omega,\gamma)$$

The parameters $\gamma$, $\epsilon_0$ are predetermined and are design specific. Typically, values of 0.001 and 0.0001 are used for $\gamma$ and $\epsilon_0$ respectively. In the above expression $|P_m|$ determine the weights of the $\delta$ spikes of the averaged spectral power density.

For particular applications, the QEF is designed by matching the power spectral density (PSD) amplitude of coded mutation signature to that of the spin-boson system described above so that stochastic and deterministic time scales match and so that the time scales couple back to noise statistics and degree of asymmetry. The method employs a fully automated iterative conjugate gradient relaxation method for Spectral matching between asymmetric base system and coded mutation signature. The actual determination of the QEF depends on the specifics of bioelectronics substrates used for actual analysis. The method is however generalizable to all or almost all arrayed embodiments. In addition, the method is highly scalable to array dimensions (as the offline design trade-space time does not matter to computational complexity). Since the system is an overdetermined coupled system, convergence criteria and stability of relaxation method directly relates to downstream resonance effectiveness.

Order Function

At step 306, the order function (OF) of ground truth is generated as follows. The order function (OF) is for ground truth wherein ground truth represents a state wherein a positive signal to noise ratio (SNR) is expected for hixel intensities of selected oxels.

A general form for the classical Order Function (OF) is $$H(\theta) = -\sum_{k=-\infty}^{\infty} h_k Z_k e^{-2\pi i k\theta}$$

where $i = \sqrt{-1}$ and $h_k \equiv \int_0^1 d\theta h(\theta)e^{-2\pi ik\theta}$ and $0 < \theta < 1$.

The following equation $$h_k \equiv \int_0^1 d\theta h(\theta)e^{-2\pi ik\theta}$$

is referred to the Diado integral.

The OF is calculated using an order match which implies the variance of the density function for a specific exponential family approaches 0 (within 0.000001–0.0001). The free energy for the density function is given by $$p(x) = \frac{1}{\sqrt{2\pi}} \int_{-\infty}^{\infty} \xi^a \xi_b e^{[i\lambda(x_a^b - x e_a^b)]} d\lambda$$

where $\xi^a$ and $\xi_b$ represent state vectors. $X_a^b$ represents the random observable in symmetric bilinear form, and $\lambda$ denotes the characteristic function.

The detailed form and the specific results for solving the system are given in D. C. Brody and L. P. Hughston, Geometry of Quantum Statistical Inference", Physics Review Letters, 77(14), pp. 2851–2855, 1996. An important aspect of the exemplary method of the invention in using the result to derive the QEF which gives unique advantages in the enhancement process.

Entrainment States

Thus the OF derivation is based in Diado's theory of multibranch entrainment of coupled nonlinear oscillators, wherein a number of different entrained states co-exist. At ground truth POBC locations, an a priori measurement of entrainment is performed (step 408). This is done by approximate Daido Integral( ) with $Z_k$=PSD maxima at regions where DST boundary>desired detection threshold. (For more information regarding the Daido Integral, see Physics Review Letters, 77(7), 1406–1411.) Premultiplier constants are used to ensure that Zk meets the following tests:

maxima power spectrum density (PSD) matches; and $L_2$ norm on even harmonics<e where e=NS-MRF Barrier assuming CSR assumptions.

The notion of entrainment states is exploited, in part, because the method treats the hixel dot spectrogram as a special case of coupled nonlinear oscillators in equilibrium. However, due to device imperfections, hybridization degradation and other limitations number of entrained binding states (i.e., incorrectly hybridized) coexist. A PSD match is desired where the OF is Z-peaked (but single peaked around each MRC-hixel). Absence of a single peak implies perfect or lack of hybridization. It also defines the resonance loci for this method (i.e., where maximum SNR enhancement) is obtained.

Ground Truth Modulation

The OF of ground truth is modulated at step 410 to yield the QEF as follows. Under controlled calibration, as stated above, maximal SNR enhancement (optimal resonance) is achieved when OF yields a single peak. It is a important design point for matching PSD of coupling spin Boson system to the synthetic QEF. The specific form of the QEF to be used is the generic OF shown above. So the exemplary method exploits two connotations of OF: (a) parametric form for the QEF (that is closer to the classical form) and (b) as exponential attractor for a dissipative system. The two OF's are then recoupled and convolved with the preconditioned dot spectrogram (see below).

The resulting QEF generated via the steps of FIG. 4 is given by:

$$QEF_{MRC_i} = \vec{H}(\vec{\theta}) = -\sum_{j=l_x}^{u_x} \sum_{k=l_y}^{u_y} \hat{h}_k|_{v_i=1,2,3} Z_k e^{-2\pi i k \theta}$$

Typically, only first three PSD peaks are considered for spectral matching.

Preferably the QEF is represented digitally using a matrix or array having the same number of elements as the dot spectrogram to be analyzed.

Phase Space Resonance Stimulus Using Palm Operators

Referring again to FIG. 2, if the dot spectrogram generated at step 206 is not a phase-space representation of the output of the hybridization chip, then it is desirable to convert the preconditioned dot spectrogram (generated at step 208) and the QEF into phase space to facilitate a phase space resonance interaction. In other embodiments, though, an amplitude-based resonance interaction is performed and hence it is not necessary to convert to phase space. In still other implementations, other types of resonance interactions may be employed. In the following, it is assumed that the dot spectrogram has phase space components and hence the following conversion steps are applied to the QEF at step 204 and similar steps are applied to the dot spectrogram following image preconditioning.

A phase embedding operator, $\Gamma$, is applied to the hixels corresponding to the coded base mutation set such that hixel values now correspond to angles and not to intensities. These values are cyclic, with absolute magnitude of the phase image having no meaning. The relative magnitudes are more significant. So if X is a phase image and a is any constant, then X+a (mod color_map_scale) is a valid descriptor for the phase image. More importantly, the difference between a max_hixel_intensity and min_hixel_intensity is 1 and not color_map_scale. The difference between phase values at two hixels i and j is X(i)−X(j) (mod color_map_scale).

The phase embedding operator is designed such that transitive closure between any two hixels is maintained, i.e., there is an accumulated phase function $\psi$ for which $$X(i) = \psi(j) \pmod{\text{color\_map\_scale}}$$

The phase values of $\psi$ accumulate rather than cycling back to 0. Note that $\psi$ can be approximated at least locally by a linear function $f$ with deviation error function err(p) having values relatively close to zero for which $$\psi(p) = f(p) + \text{err}(p)$$

This function $f$ is the analog of an amplitude image having a constant intensity and err(.) is the analog of the deviation from this constant amplitude. It is assumed that err(p) never crosses a phase discontinuity and can be treated like a real-valued function. If values are computed for this deviation function err(.), then |err(p)| would specify an intensity image whose local maxima might indicate detection of expressed oligonucleotides of interest.

Each phase angle corresponds to a point on the unit circle in the coordinate lane. This is a one-to-one mapping in both direction. Let V be the mapping that takes a phase angle into the corresponding vector on the unit circle. Let I be the inverse mapping that takes a vector on the unit circle back into the corresponding phase angle. V(f(p)) is thus a vector valued function which has no associated phase discontinuity. V can be averaged over a region without the problems associated with directly averaging phase angles.

Given a rectangular neighborhood N(p,m,n) of the hixel p, let v be the vector which is the average of all the values of V(f(p)) in this region and let |v| be the magnitude of this vector. Clearly |v| must lie between 0 and 1, inclusive. Moreover, |v| is a measure of the dispersion of the phase angles. If |v|=1, then all the vectors in the region N(p,m,n) are equal to v. If |v|=0, then the vectors are distributed more or less uniformly about the unit circle and there is no "average" phase angle. If |v|0, then v/|v| is a vector on the unit circle and I(v/|v|) can be defined to be the "average" phase angle ave(f,p,m,n). Clearly, the closer |v| is to 1, the tighter the clustering of the vectors about v/|v| and the greater the certainty that this is a meaningful average value. The important characteristic is that this average will tolerate phase with data noise.

If the line is taken which is perpendicular to the vector v and passes through the point v, then this line will specify a chord of the unit circle. The arc of the unit circle which corresponds to this chord is the region from which the "average" vector comes. The length of this arc is 2*arccos ($|v|$). Thus, to ensure that the "average" vector lies in a single quadrant or a 90 degree arc:

$$|v|=\cos(45 \text{ degrees})=0.7071$$

$|v|$ is referred to herein as the average magnitude and the minimum acceptable value for this average magnitude is referred to as minimum average magnitude.

Averaging Phase Input: Let f be a phase image, F the corresponding accumulated phase function, and L+e=F be as described above. Assume that m and n are odd integers so that N(p,m,n) is a symmetric mXn rectangle of hixels with p in the exact center. Since L is linear and N(p,m,n) is symmetric about p, the average of L over N(p,m,n) will be L(p). Since e=F−L, the average of e over should be N(p,m,n) to be close to 0. Hence, approximately, $$\begin{aligned} \text{ave}(F, p, m, n) &= \text{ave}(L+e, p, m, n) \\ &= \text{ave}(L, p, m, n) + \text{ave}(e, p, m, n) \\ &= L(p) + \text{ave}(e, p, m, n) \\ &= L(p) \end{aligned}$$

Since f(p)=F(p)(mod), the average values of these two functions over N(p,m,n) should also satisfy this relationship and hence, approximately, $$\begin{aligned} \text{ave}(f, p, m, n) &= \text{ave}(F, p, m, n)(\text{mod}) \\ &= L(p)(\text{mod}) \end{aligned}$$

In other words, it is reasonably expected that ave(f,p,m,n) recovers an approximation to the underlying linearity. If this is valid, then $$|\text{ave}(f,p,m,n)-f(p)|$$

is a measure of the deviation of f at p from this underlying linearity and these values form an intensity image whose large values and local maxima reasonably correspond to mutations of interest.

A possible disadvantage of this approach is that it may be valid only if the phase values being averaged are all within a single phase cycle and, preferably, within a fraction of a phase cycle (e.g., 120 degrees). If the available phase image is too grainy, it may not be possible to average over a large enough rectangle. In this case, it is probably necessary that there be some larger scale linear regularity which extends over at least several consecutive phase cycles. The remaining sections presents alternatives based on this assumption.

Define the first vertical difference of a phase image f to be $$dv(f,p)=f(i+1,j)-f(i,j)(\text{mod})$$

where p=(i,j). Similarly, define the first horizontal difference of a phase image f to be $$dh(f,p)=f(i,j+1)-f(i,j)(\text{mod})$$

These both define new phase images derived from f and are discrete analogs to the first derivative. The range of values for dv and df are also from −180 to +180.

Let F be the accumulated phase function corresponding to f and let L+e=F be as described above. For the sake of convenience, assume that p is translated to the origin so that p=(0,0). The linear function L is expressed as $$L(i,j)=V*i+H*j+K$$

for some constants V, H, and K. If L is a reasonable approximation to F, then it is expected that the first vertical difference of f to be an approximation to the slope V and the first horizontal difference of f to be an approximation to the slope H. Hence it is possible to estimate V and H by averaging dv and dh over some appropriate rectangle centered at p. Let $$V'=\text{ave}(dv(f,p),p,m,n)$$

$$H'=\text{ave}(dh(f,p),p,m,n)$$

be these estimates. Note that these are phase averages. Probably m and n should be chosen so that m/n is roughly equal to H'/V'. This ratio would imply that the total phase accumulation across the rectangle N(p,m,n) is about the same in both the vertical and horizontal directions. For example, the rate of change of phase along the i-axis (vertical) may be twice the rate of change along the j-axis (horizontal). In this case, a 5×10 rectangle of hixels may turn out to be the most appropriate neighborhood.

If a good estimate K' is computed for K, then an approximation to L is:

$$L'(i,j)=V'*i+H'*j+K'$$

If L' is a good enough approximation to L and F is linear enough, then the accumulated phase function F is reconstructed as follows:

$$e'(p)=f(p)-L'(p)(\text{mod})$$

and $$F(p)=L'(p)+e'(p)$$

Note that this may require that the error function e' never deviate far enough from 0 to cross a phase discontinuity.

With an accumulated phase function F now explicitly computed on some rectangle N(p,m,n), standard numerical analysis techniques are applied, such as linear regression, to find a function L" which best approximates F over this rectangle. The value $$\text{dev}(f,p,m,n)=|F(p)-L''(p)|$$

can be taken as a measure of the deviation at p of the image f from its "expected" value at p. In particular, this defines a new image whose values are intensities rather than phase angles and whose local maxima can be analyzed.

To compute a good estimate K' for K in order to determine the function L', choose a good estimate of K' to be a phase value between −180 and +180 which minimizes the average value over the rectangle N(p,m,n) of either $$|f(p)-L'(p)(\text{mod})|$$

or $$(f(p)-L'(p)(\text{mod}))^2$$

If the accumulated phase function F corresponding to the phase image f is approximately a linear function and, as a result, the first differences are approximately constant, then the first differences of the first differences should be approximately 0.

Define the second vertical difference of a phase image f to be $$d2v(f,p)=[f(i+1,j)-f(i,j)(\bmod)]-[f(i,j)-f(i-1,j)(\bmod)](\bmod)$$

and the second horizontal difference of a phase image f to be $$d2h(f,p)=[f(i,j+1)-f(i,j)(\bmod)]-[f(i,j)-f(i,j-1)(\bmod)](\bmod)$$

This corresponds to an indexing of a one dimensional difference table that looks like the following:

```
a0  a1  a2  a3  a4  a5  a6
  b0  b1  b2  b3  b4  b5
    c1  c2  c3  c4  c5
``` where b0=a1−a1, b1=a2−a1, ... and c1=b1−b0, c2=b2−b1, ...

Let F=L+e be define as earlier. If e were identically 0, then F would be linear and both second differences d2v and d2h would also be identically 0. If e is not identically 0, the second differences will necessarily also deviate from 0, however, not necessarily in the same place as e. If |e| attains a local maximum at a hixel p and this is associated with a very localized deviation from 0, as would be expected of a signal from a mutation of interest, then d2v and d2h should also deviate from 0 fairly nearby to p.

The deviation in d2v and d2h associated with a deviation in |e| may be spread out over a number of hixels. This will not only make it harder to detect a significant change in d2v and d2h but also make it harder to locate the center of this change using a local maxima finding filter. It may be possible to compensate for this by averaging d2v and d2h or |d2v| and |d2h| over rectangular regions N(p,m,n). This should tend to sharpen the peaks in d2v and d2h. Correlating several different images generated using d2v and d2h may also help with center finding since the correlation algorithm will automatically average nearby local maxima.

Thus a method for achieving induced coupling for phase space has been described. Repeatability of the overall method hinges significantly on the aforementioned coupling as it induces analytic redundancy via complex information fusion at constant feed forward computational cost. Hence, the coupling is advantageous for at least two reasons: 1) it applies to any microarray device that may provide a phase or cyclical (modulo) input as opposed to amplitude input; and 2) it is important for use with active hybridization devices which will have an element of built in control that will have a phase representation. The coupling is actually introduced into the exemplary method in three possible ways.

(a) if the entire resonance computation proceeds in the phase space as opposed to amplitude space. Then it is necessary to transform QEF and post-hybridization microarray output to phase space. The coupling material provides the transformations to do so.

(b) if the microarray output is already in the phase space then it will only be applied to convert the QEF.

(c) if different oxels are designed to solve for different aspects of the analysis, the coupling permits a combination of outputs to reach a final conclusion.

Entrained states are employed, in part, to precisely compensate for that point. So already in the method synthetic decomposition and coupling are provided. But it is used to reject spurious candidates as opposed to "light up" more oxels with potential match.

Again the step of converting to phase space may be optional depending upon the implementation and is applied, if at all, after preconditioning and/or before introducing the QEF to the resonant interaction step.

Also, a major limiting restriction in QSR that is avoided by the exemplary method pertains to matching the stochastic and deterministic time scales in "domain system" and the external coupling asymmetric dynamical system, since this has limited applicability to continuous data. By replacing the time scale match requirement with ensemble spatial statistics (structure of oligonucleotide itself) expressed via the aforementioned generators an entirely new class of analysis for discrete systems is enabled By deriving the condition that labeled oligonucleotide chains need to satisfy to maximize QEF generator capacity, a properly constructed and conditioned QEF will be able to extract and enhance an entire class of mutations over and beyond single mutation detectability.

The resulting phase-space representation of the resonance stimulus generated at step 204 is given by:
The resonance stimulus is computed by applying $$\Phi_{resonance\ stimulus} = (D2h(QEF_{MRC\_i}) \otimes_{mod_n} D2v(QEF_{MRC\_i})\ \text{for all QEF subarray elements.}$$

As with the QEF, the resonance stimulus pattern is preferably represented digitally using a matrix or array having the same number of elements as the dot spectrogram to be analyzed.

Generation of the Dot Spectrogram

Continuing with the detailed description of the steps of FIG. 2, as noted a dot spectrogram is generated at step 206 for a sample from an N by M DNA chip array wherein an element of the array is an "oxel": o(i,j). A 6-σ manufacturing process accuracy in microarray design is assumed. Each array cell amplitude is given by $\Phi(i,j)$ for i: 1 to N, and j: 1 to M. Let $\psi(i,j)$ denote the a priori known oligonucleotide given by $[\alpha_0 \alpha_1 \ldots \alpha_k]$, where $\alpha=\{A,C,T,G\}$ base associated with each array cell [a,b] where $10 \leq k \leq 25$. The complimentary strand, derived from unknown sample is denoted by $\vec{\Psi}(i,j)$.

The post-hybridization microarray is treated mathematically using the machinery of equations with aftereffect. Each hixel given by $\Phi(i,j)$ is represented as a cluster of dynamical systems of potentially [CB] correctly bound, [UB] unbound, [PB] partially bound and [IB] incorrectly bound. Thus $[CB]_{\Phi(i,j)}+[UB]_{\Phi(i,j)}+[PB]_{\Phi(i,j)}+[IB]_{\Phi(i,j)}=T_{\Phi(i,j)}$ within 0.0001%.

The model analytic for the estimated fluorescence activity $\Psi$ in a hixel $h_{(i,j)}$ is given by $$\dot{\Psi}_{h_{(i,j)}}(t) = \Theta_{h_{(i,j)}}(t, \Psi_{t,h_{(i,j)}}, \dot{\Psi}_{t,h_{(i,j)}}),\ t\ t_0\ \text{(hybridization start time).}$$

The fluorescence stabilization section is given by $$\Psi_{t,h_{(i,j)}} = \Psi_{h_{(i,j)}}(t+\delta),\ \delta \leq 0;$$

And the rate of fluorescence stabilization is expressed via $$\dot{\Psi}_{t,h_{(i,j)}} = \dot{\Psi}_{h_{(i,j)}}(t+\delta),\ \delta \leq 0;$$

While $\Theta \Psi_{t,h_{(i,j)}} = \Psi_{h_{(i,j)}}(t+\delta),\ \delta \leq 0$; the system is assumed to be memoryless, i.e., $\Theta$ is ergodic.

The resulting dot spectrogram generated at step 206 is given by:

$$\Phi(i,j)$$

Preconditioning of the Dot Spectrogram

Figure 5:
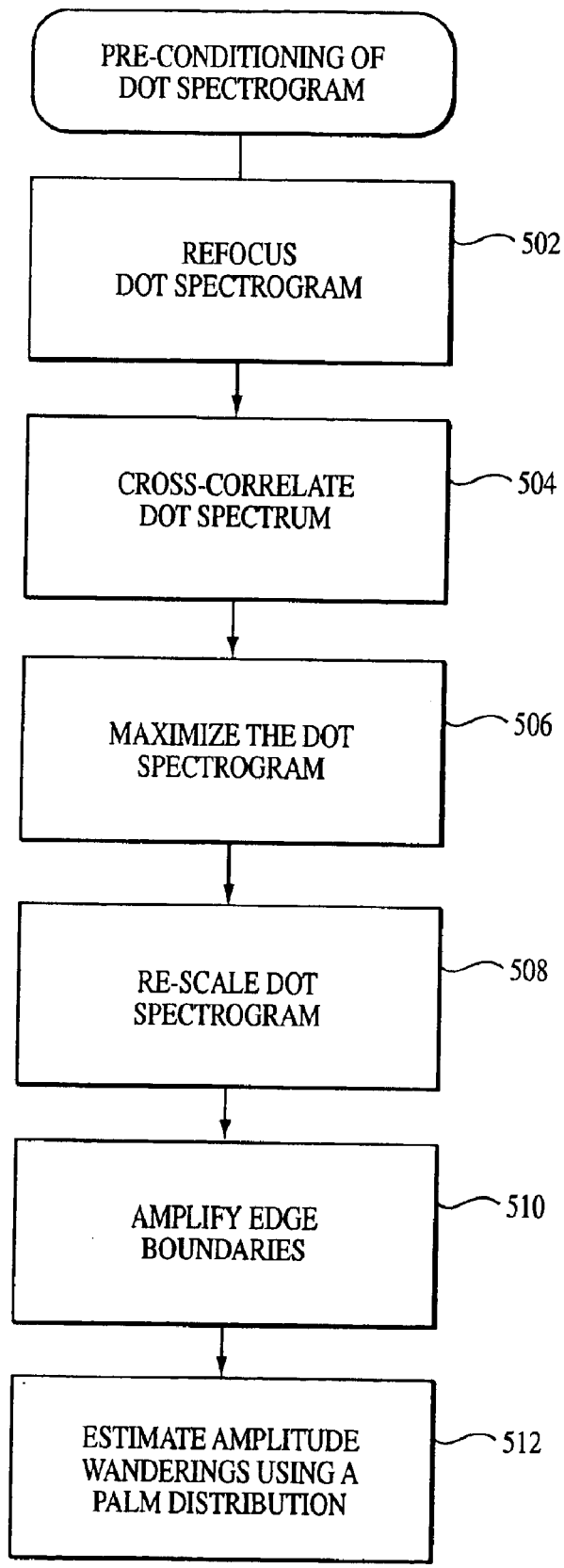
FIG. 5 is a flow chart illustrating an exemplary method for preconditioning the output of a hybridized DNA microarray for use with the method of FIG. 2.

With reference to FIG. 5, the dot spectrogram $\Phi(i,j)$ is preconditioned by performing the following steps. First, at step 502, the dot spectrogram is refocused to yield a refocused dot spectrogram. Then, at step 504, a cross-correlation convolution operation is performed to yield a correlated refocused dot spectrogram. A local maxima filter $\upsilon$ is then applied at step 506 to the correlated refocused dot spectrogram to yield a maximized dot spectrogram. The maximized dot spectrogram is re-scaled at step 508 to yield a uniformly re-scaled dot spectrogram. The uniformly re-scaled dot spectrogram is then further re-scaled at step 510 by amplifying local edge hixel boundaries of the uniformly re-scaled dot spectrogram to yield a globally re-scaled dot spectrogram denoted by $\Phi(i, j)$. Also, amplitude wanderings within the globally re-scaled dot spectrogram are estimated at step 512 for use downstream.

The steps of FIG. 5 result in a dot spectrogram tessellation (DST) operator. Purpose of DST Operator is to determine idealized ensemble boundaries for forcing downstream resonant action. Typically, in signal processing applications, high pass or band pass spatial filtering is implemented to enhance SNR in dot spectrogram matrix. Alternate methods apply a combination of Laplacian or other edge detection filters apply to enhance signal from arrays cells with a higher hybridization concentration from those of the adjacent cells. These SNR enhancement methods however work only with positive or zero-SNR. Since SNR in general is negative in our case (ultra-low target DNA concentrations), these methods in effect amplify noise or further blur the hixel boundaries.

With the exemplary method, a new technique is used to amplify highly local morphological variations in the overall dot spectrogram matrix. A filter $\zeta$ is applied to the normalized amplitude dot spectrogram matrix $\Phi$, for all combinations $\pm i \pm j \pm k$ where k is typically ranges from 0 to 2.

Refocusing the Dot Spectrogram

Refocusing of the dot spectrogram at step 502 to yield a refocused dot spectrogram is performed by determining a locally averaged amplitude sub-array represented by $\Omega$, then for each value of i,j and k, where k ranges from 0 to 2: determining a local standard deviation $\sigma$ over a $(2k+1) \times (2k+1)$ hixel neighborhood centered at (i,j) and applying a filter $\zeta$ to the dot spectrogram $\Phi$, for all combinations $\pm i \pm j \pm k$.

$\sigma$ is calculated by $$\sigma^Z = \sqrt{\sum_{i-2}^{i+2}\sum_{j-2}^{j+2}(\Phi(i,j)-\Omega^z)^2}$$

The calculation of $\Omega$ is independent of the oxel layout. From a preconditioning effectiveness standpoint, a best case design corresponds to a completely random oxel layout in terms of $\tilde{O}$-value for adjacent oxels. The worst case corresponds to $\tilde{O}$-value separation of 1 among adjacent oxels. The oxel, $o(i,j)_Z$, centered at (i,j) comprises of complementary oligonucleotides, corresponding to a mutation of interest over the set Z. Loci, r, for averaging amplitude ranges from $\pm 5$ oxels to $\pm k$ oxels depending on ($\tilde{O}$-value mod $4^k$) separation. $\Omega_1^Z$ then is computed using $$\Omega_1^z = \sum_{i-r}^{i+r}\sum_{j-r}^{j+r}\frac{\Phi(i,j)}{(2r+1)^2} \vee Z.$$

When the averaging loci for multiple mutations of interest overlaps, then composite loci, r' is bounded by a rectangle whose top left hand and bottom right hand corner coordinates are given by $[i_{min}-k-1, j_{max}+k+1]$ and $[i_{max}+k+1, j_{min}-k-1]$ where $i_{min}, i_{max}, j_{min}$ and $j_{max}$ correspond to the ordinate and abscissa for the oxel mutations with overlapping loci.

$\zeta$ given by:

$$\Phi(i,j)'_1 = \Phi(i,j) - \kappa.[\Omega(\Phi(i,j),k)/\sigma(\Phi(i,j),k)] \forall i,j$$

The preceding expression captures local ensemble deviation from dot spectrogram average. The design parameter $\kappa$ is computed offline based on specific bio-molecular signatures of interest. The suffix 1 denotes iterative index for a cross-correlation convolution operation to be applied after global refocusing.

A uniform dot spectrogram resealing can be achieved by applying $\alpha$. $\check{o}(I,j)$ where $\alpha$ can be either a constant or a functional. This operator selectively enhances those hixels and ensemble boundaries whose intensity exceeds the local average by more than $\kappa$ prespecified standard deviations.

$\kappa$ is a predetermined constant computed offline based on microarray fluorescence or chemiluminiscence sensitivity.

$$\kappa = \exp\left(-4\sqrt{\frac{\min(\text{oligonucleotides/oxels required for flourorescent detection})}{\text{total}(\text{oligonuucleotides/oxel})}}\right)$$

The suffix 1 denotes an iterative index for a cross-correlation convolution operation to be applied after global refocusing.

Cross-Correlation of the Dot Spectrogram

The cross-correlation convolution operation of step 504 to yield a correlated refocused dot spectrogram is performed by convolving the refocused dot spectrogram with an apriori-chosen restricted field obtained using a strongly dissipative dynamical system. Dissipative dynamical systems are those which define a forward regularizing flow in an adequate phase space containing an absorbing set. An absorbing set is a bounded set that attracts all bounded solutions in finite time at an exponential rate. Since we exploit a strongly dissipative system, the absorbing set is required to be unique compact set that is both positively and negatively invariant under the flow, it attracts all flows.

Conceptually, the post-hybridization hixel denotes a projection of the flow field that is absorbed by the coupling system. Since we couple with an absorbing set, this stage yields significant SNR enhancement.

In general, the convolving field can be constructed using Kuramoto-Sivashinsky equation, 2D Navier-Stokes equation or some forms of Reaction-Diffusion equations. The dot spectrogram subarray around the oxel detecting mutation of interest can be cross-correlated with any dissipative dynamical system. In summary this step exploits proven classes of mathematical system or exponential attractors. By definition exponential attractor is an exponentially contracting compact set with finite fractal dimension that is invariant under the forward flow.

In the exemplary implementation, the following is performed to achieve the cross-correlation. A synthetic system of the form is assumed, whose evolution equation is given by $$u_t + Au + R(u) = 0$$

$$u(0) = u_0$$

where A is a positive self-adjoint operator with compact inverse and nonlinear term R satisfies the order match condition in step 306 in FIG. 3.

The functional formulation of 2D Navier-Stokes equations for incompressible fluid flow is chosen as the coupling system It is given by $$u_t + \nu Au + B(u,u) = f,$$

$$u(0) = u_0$$

where $A = -P_H \Delta$ is the Stokes operator, $B(u,u)$ stands for the non-linear term (u. $\Delta$u) projected to the underlying Hilbert space H, f is the volume force projected to the same Hilbert space and v is the viscosity term. To meet the incompressibility condition the following Hilbert space is assumed to set the initial value problem $$H = \left\{ u \in L^2(Q)^2 : \text{div } u = 0, \int_Q u(x) dx = 0, u_i |_{x_i=L} = u_i |_{x_i=0}, i = 1, 2 \right\}$$

and $$V = \{ u \in H^1(Q)^2 : u \in H \}$$

where Q is the square $[0,L] \times [0,L]$. The mathematical domain of the Stokes operator is given by $$D(A) = H^2(Q)^2 \cap V$$

Galerkin Approximation can be used to approximate the exponential attractor for the system The above system with periodic boundary conditions admits an exponential fractal attractor M in B whose dimensions can be estimated using $$d_F(M) \leq cG^2(\log G^4 \nu \lambda_1 + 1)$$

where G is the Grashoff number given by $$\frac{|f|}{\nu^2 \lambda_1}$$

and c is a constant that depends on the shape factor. $\lambda_1$ denotes the positive eigenvalue of A.

The rate of convergence of this system can be computed as well.

The exponential attractor is then coupled with the post-hybridization dot spectrogram subarray The exponential attractor is discretized over the grid that corresponds to the refocused amplitude subarray associated with a mutation and estimated above.

The actual convolution of the two systems is then given by $$\frac{1}{r^2} \sum_i \sum_j \exp(-S[i,j] * \Phi(i,j))$$

This process is computed for each oxel associated with the loci of a specific mutation of interest.

Maximizing the Dot Spectrogram

Step 506 for applying a local maxima filter $\eth$ at to the correlated refocused dot spectrogram to yield a maximized dot spectrogram is then implemented as follows. The local maxima filter is defined by $$\Omega' = \Phi'(i,j) \times \eth(i,j)$$

wherein $\eth(I,j) = 1$ if $\Phi(i,j)'$ is a local maxima (or defines a local maxima ensemble with several neighboring hixels with same amplitude intensity); and wherein $\eth(I,j) = 0$ otherwise.

Re-Scaling the Dot Spectrogram

The maximized dot spectrogram is rescaled at step 508 to yield a uniformly re-scaled dot spectrogram by applying an operator $\alpha$. $\eth(I,j)$ where $\alpha$ is either a predetermined constant or a predetermined functional.

$\alpha$ is set so as to uniformly scale the convolved dot spectrogram to $1/(1+\exp(-MIN_{INT}/2))$ to $1/(1+\exp(MAX_{INT}/2))$. Where $[MIN_{INT}, MAX_{INT}]$ refers to the dynamic range of the microarray.

The uniformly re-scaled dot spectrogram is itself then rescaled at step 410 by amplifying local edge hixel boundaries of the uniformly re-scaled dot spectrogram to yield a globally re-scaled dot spectrogram. This is achieved by 1) determining the zero mean amplitude for the uniformly re-scaled dot spectrogram; 2) applying a logarithmic rescaling function $\wp$ around the zero mean amplitude; and 3) merging the local maxima into a single local maximum half way in between.

The logarithmic rescaling function is generated by generating an expansion sequence of nonnegative numbers and by generating an expanded dot spectrogram tessellation for $\Phi$.

The expansion sequence is generated as follows:

$$\{\wp\} = \wp_0, \wp_1, \wp_2, \ldots$$

which is strictly decreasing until it reaches zero and thereafter is equal to zero by using:

$$\aleph(n) = \begin{vmatrix} 2^{n-1} & \text{for } n \geq 0 \\ 0 & \text{for } n < 0 \end{vmatrix}$$

The expanded dot spectrogram tessellation for $\Phi$ (which is represented by DST($\Phi$)) is generated using:

$$DST(\Phi) = \wp(D(\phi_i, \phi_k))$$

wherein $D(\phi_i, \phi_k)$ is a shortest possible discretized fluorescence amplitude separation between a pair of hixels $\phi_i, \phi_k$ wherein $\phi_k$ is a local maximum.

The local maxima are merged into a single local maximum half way in between for downstream hixel-to-ensemble and ensemble-to-ensemble operations on hixel clusters using the sequence $$\max\{\aleph(c) - \aleph(m), 0\}; m = 0, 1, 2, \ldots$$

where c is some positive integer constant.

Additional details are as follows, for any pair of dot spectrogram hixels, $\phi_i$ and $\phi_j$, let the discretized fluorescence amplitude separation between them be denoted by $D(\phi_i, \phi_j)$. So, $D(\phi_i, \phi_j)=0$ if and only if $|\phi_i-\phi_j|\leq C$ where $C=Max(\wp(\Phi(i,j)))-Min(\wp(\Phi(i,j)))/N$ and $D(\phi_i,\phi_j)=1$ if and only if $\phi_i$ and $\phi_j$ are adjacent to each other on the normalized scale, but not identical, i.e., $|\phi_i-\phi_j|\leq 2C$. Let $\phi_k$ be a local maxima image for some other dot spectrogram realization $\Phi(i,j)"_l$. Define $D(\phi_i, \phi_k)$ to be the shortest distance possible from hixel $\phi_i$ to some hixel $\phi_k$ which is a local maximum. Clearly, $D(\phi_i, \phi_k)=0$ if and only if $\phi_k$ is a local maximum and $D(\phi_i, \phi_k)=1$ if and only if $\phi_k$ is not a local maximum but is adjacent to some local maximum.

The an expansion sequence is thus defined to be any sequence of nonnegative numbers $\{\wp\}=\wp_0, \wp_1, \wp_2, \ldots$ (as mentioned above) which is strictly decreasing until it reaches zero and thereafter is equal to zero. For example, $\{\wp\}=15, 11, 5, 2, 1, 0, 0, 0, 0, \ldots$ If $\Phi$ is a local maxima DST and $\{\wp\}$ is an expansion sequence, then the expanded DST($\Phi$) is defined as $DST(\phi)=\wp(D(\phi_i, \phi_k))$ $\aleph$: Z→Z on integers is useful for defining expansion sequences. A key property of this sequence is that given only the value of the sum s=p+q, where p and q are any numbers from this sequence, then we can always determine the values of the two original summands p and q. For example, choose the expansion sequence to be:

31, 15, 7, 3, 1, 0, 0, 0, 0, ... (generated by $\aleph$(5−i):for i=0, 1, 2, ...)

and let $DST_A$ and $DST_B$ be two DST realizations "expanded" using this sequence. This unique summation property ensures that a threshold value can be chosen for the DST summation $DST_A+DST_B$ so that the resulting realization retains only those local maxima in the two images which are within bounded intensity of n of each other. This expansion sequence preserves the individual local maxima from each of the two realizations.

For downstream hixel-to-ensemble and ensemble-to-ensemble operations on hixel clusters the local maxima are merged into a single local maximum half way in between using the sequence using $max\{\aleph(c)-\aleph(m), 0\}; m=0, 1, 2, \ldots$ where c is some positive integer constant.

In the alternative, a Dirichlet tessellation operator or a Delaunay triangulation operator are then applied to perform gradient refocusing rather than steps 502–510.

Estimation of Amplitude Wanderings

Amplitude wanderings are estimated at step 412 within the enhanced dot spectrogram. The estimate is performed by applying a Palm Distribution operator to the globally re-scaled dot spectrogram to capture amplitude wanderings and transitions at element, neighboring pair and local ensemble levels. The application of the Palm Distribution operator generates bounds that are used to accommodate degradation of hybridization over time. Essentially the estimate exploits the use of generator functions to capture stochastic variability in hybridization binding efficacy and draws upon results in stochastic integral geometry and geometric probability theory.

Geometric measures are constructed to estimate and bound the amplitude wanderings to facilitate detection. In particular we seek a measure for each mutation-recognizer centered (MRC-) hixel that is invariant to local degradation. Measure which can be expressed by multiple integrals of the form $$m(Z) = \int_Z f(z)dz$$

where Z denotes the set of mutations of interest. In other words, we determine the function f(z) under the condition that m(z) should be invariant with respect to all dispersions $\xi$. Also, up to a constant factor, this measure is the only one which is invariant under a group of motions in a plane. In principle, we derive deterministic analytical transformations on each MRC-hixel., that map error-elliptic dispersion bound defined on $R^2$ (the two dimension Euclidean space—i.e., oxel layout) onto measures defined on R. The dispersion bound is given by $Log_4(\hat{O}_{(i,j)}|^2)$.

Such a representation uniqueness facilitates the rapid decimation of the search space. It is implemented by instantiating a filter constructed using measure-theoretic arguments. The transformation under consideration has its theoretical basis in the Palm Distribution Theory for point processes in Euclidean spaces, as well as in a new treatment in the problem of probabilistic description of MRC-hixel dispersion generated by a geometrical processes. Latter is reduced to a calculation of intensities of point processes. Recall that a point process in some product space E X F is a collection of random realizations of that space represented as $\{(e_i, f_i), |e_I \in E, f_i \in F\}$.

The Palm distribution, $\Pi$ of a translation $(T_n)$ invariant, finite intensity point process in $R^n$ is defined to the conditional distribution of the process. Its importance is rooted in the fact that it provides a complete probabilistic description of a geometrical process.

In the general form, the Palm distribution can be expressed in terms of a Lebesgue factorization of the form $E_P N^* = \Lambda L_N X \Pi$ Where $\Pi$ and $\Lambda$ completely and uniquely determine the source distribution P of the translation invariant point process. Also, $E_P N^*$ denotes the first moment measure of the point process and $L_N$ is a probability measure.

Thus we need to determine $\Pi$ and $\Lambda$ which can uniquely encode the dispersion and amplitude wandering associated with the MRC-hixel. This is achieved by solving a set of equations involving Palm Distribution for each hybridization (i.e., mutation of interest). Each hybridization is treated as a manifestation of a stochastic point process in $\Re^2$.

In order to determine $\Pi$ and $\Lambda$ we have implemented the following measure-theoretic filter:

Determination of $\Pi$ using integral formulae constructed using the marginal density functions for the point spread associated with MRC-hixel(i,j)

The oligonucleotide density per oxel $\sigma_{m(i,j)}$, PCR amplification protocol $(\rho_m)$, fluorescence binding efficiency $(\eta_m)$ and imaging performance $(\bar{\omega}_m)$ provide the continuous probability density function for amplitude wandering in the m-th MRC-hixel of interest. Let this distribution be given by $\wp(\rho_{m(i,j)}, \sigma_m, \eta_m, \bar{\omega}_m)$.

$\wp(\rho_{m(i,j)}, \sigma_m, \eta_m, \bar{\omega}_m)$

The method requires a preset binding dispersion limit to be provided to compute $\Lambda$. The second moment to the function at SNR=0 condition is used to provide the bound.

Determination of Π
Obtained by solving the inverse problem $$\Pi = \Theta * P$$

where $$P = \int_{\tau_1}^{\tau_2} \wp(\rho_{m(i,j)}, \sigma_m, \eta_m, \varpi_m) \partial \tau$$

where $\tau_1$ and $\tau_2$ represent the normalized hybridization dispersion limits. These number are empirically plugged in. We choose 0.1 and 0.7 respectively to signify loss of 10%–70% hybridization.

Also, Θ denotes the distribution of known point process. We use the form $1/(1+\exp(\wp(\ldots)))$ to represent it.

Ultimately, the final preconditioned (or enhanced) dot spectrogram generated by the step of FIG. 5 is represented by:

$$\Phi(i,j).$$

Resonant Interaction

Referring again to FIG. 2, at step 210, the resonant interaction between the QEF and the preconditioned dot spectrogram is performed until a pre-selected degree of convergence is achieved.

$$a\dot{\bar{u}} = -\frac{\partial V(\bar{u})}{\partial \bar{u}} + \bar{\Psi}(t) + QN(t)$$

The resonance interaction proceeds by iteratively calculating a resonance equation until convergence is achieved.

More specifically, the following resonance equation is iteratively calculated.

In the above equation V(u) is the actual precondition, refocused MRC-hixel subarray. So a stable equilibrium state (microarray) is transformed and modulated with the QEF, i.e., mathematically destabilize it to achieve a nonlinear resonance point.

In the forgoing, "a" is a constant <<fluorescence decoherence timescale(s). State variable u corresponds to non-stationary Markov random field (NS-MRF). Y(t)=A sin (wt+t) where t is a small random phase factor. "A" is a gain function (control parameter that influences convergence rates). "t" denotes integration timestep. QN(t) corresponds to the log (PSD maxima) of the ground truth order function summed over all regions of interest. More precisely, QN(t) is reverberation projection (at some instant t prior to resonant convergence) for the coupled Ofs discussed above in relation to step 204.

The Palm generators are used as additive correction terms to the potential gradient to compensate for uncertainty and post hybridization decay. The actual dynamics is given by V(u, Π, λ).

The resonant iteration is terminated when $$\text{Log} \frac{|U(t+1) - U_{f\lambda[AVG]}|}{|U(t) - U_{f\lambda[AVG]}|} \geq 1$$

or when iteration counter t exceeds $10^3$ (digital approximation to analog dynamics).

In this method the output readout from the resonance interaction is trivialized to deliver point-of-care (POC) diagnostics systems. After exponential SNR enhancement (i.e., resonance) only those k MRC-hixels will have an amplitude which are actually present in the unknown target sample.

In the event no resonance is achieved during step 210, a new QEF (corresponding to a new mutation of interest) is selected and the method reinitializes to the original DS as computed in step 508 in FIG. 5. This technique, referred to herein as a "software programmable QEF flush control methodology", of reinitializing the dot spectrogram and using a new QEF leads to a new cycle through a signal sorter for rapid single-/multi-point gene/mutation sorting. It is amenable to RF, electronic as well as optoelectronic QEF loading to microelectronics computing backplane, microarray readout and analysis backplane itself optoelectronically or electronically bonded to bioelectronic substrate. Furthermore the method can be implemented on offline miniature custom VLSI/palmtop/desktop setup. The QEF is also implementable in electronic, optoelectronic, bionic and ionic COTS/custom device physics. In the event the chip is designed such that complementary oligonucleotides for several mutations are spatially well spaced out that multiple QEF can be introduced to stimulate the system at the same time, then a logical "OR"ing of the resonance output is used to reach the detection decision.

Also, note that a chip fabricated to implement the exemplary method can work in two ways: a) seek all mutations of interest simultaneously; or b) seek all mutations of interest serially. An advantage of (a) over (b) is computational speedup. An advantage of (b) over (a) is serendipity, i.e., in method (a) only those mutations are resonantly amplified that are detection candidates. Everything else is likely suppressed or decimated. In (b) multiple resonant outputs can be accepted. By accepting multiple peaks for the OF the method can actually accept $2^{nd}$ order, $3^{rd}$ order entrained states, where order implies hamming distance to the mutation of interest in terms of base pair labels and locations. This can be used to theoretically accept entire families of derived mutations.

Preferably, the resonance interaction is performed digitally by applying a matrix representative of the resonance equation to a matrix representative of the resonance stimulus in combination with a matrix representative of the dot spectrogram.

The final result of step 210 is a set of hixel locations wherein resonance has occurred identified by row and column number (i,j).

Resonance Output Interpretation to Identify Diseases

Once resonances peak are observed in specific hixel locations of the preconditioned dot spectrogram at step 210, the hixel addresses (k,l) of those locations are mapped at step 212 into the oligonucleotide table mentioned above (which contains the oligonucleotide sequences associated with hixel locations) to thereby identify the mutations, if any, present in the sample being analyzed. This is a simple table look-up resulting in a direct readout of the mutations. For a custom POC diagnostic sensor only those hixels which relate to mutations or expressed products of interest are stored in the table.

At step 214, the mutations identified at step 212 are then mapped into the mutations table mentioned above (which contains the diseases associated with the mutations) to thereby identify the diseases, if any, present in the sample being analyzed. This is also a simple table look-up resulting in a direct readout. Again, for a custom POC diagnostic sensor only those mutations which relate to diseases of interest are stored in the table.

More specifically, at steps 212 and 214, the resonant output interaction is interpreted to yield a set of confirmed mutations as follows:

MRC-hixel$_i^Z$=o(h(k,l)) where o is some hashing function or table look-up. The step will readout the oligonucleotide sequence from a table that has encoded the microarray. Note that this mapping also operates to map the confirmed mutations to known diseases associated with the pre-selected set of mutations of interest to identify diseases, if any, indicated by the DNA sample (step 214). Note also that no probabilistic inferencing, exploitation of learning or nonlinear mapping is required to interpret the resonance output. Rather interpretation is rendered very straightforward thereby requiring only a low-cost hardware implementation with simple software to implement steps 212 and 214. So an important aspect of the exemplary method is to accurately and robustly detect specific oligonucleotide sequences in the target sample. Subsequent association to understood genomics pathways is trivialized.

Diagnostic Confirmation

Finally, the diagnosis generated by step 214 is confirmed at step 216 by taking the identified diseases and solving in reverse for the associated QEF and then comparing the associated QEF's with ones expected for the mutations associated with the identified diseases to verify correspondence and, if correspondence is not found, then a new set of mutations of interest are selected and all steps repeated.

In other words, this step maps detected mutations and expressed genes to a diagnostic assessment. This is a probabilistic or deterministic step, depending upon the genomics of the specific disease. It is represented as Diagnosis$_{P\ FA->0=\phi}$(mutation$_i$, mutations$_j$, ... mutation$_l$)

Where $\phi$ is the specific diagnostic model associated with a medical condition of interest.

Step 216 is a double check mechanism adopted to confirm multi-factorial diseases where the biochip encodes complex genomics.

Alternative Embodiments

What has been described thus far is an implementation whereby a phase-space resonance interaction is performed. This implementation, which may also be referred to as a "mixed-mode phase shifted mode" is particularly effective for automatically extracting an entire class of mutations that may be manifested in a hybridized element. In general, the mixed-mode provides polymorphism in induced couplings for QEF design which delivers repeatability on analysis whereby mutation signatures of interest are simultaneously coupled to many base "dynamical systems" with a single phase-embedding operator. Other resonance coupling interactions may be exploited as well. Other examples of couplings, other than phase-based, are "additive coupling mode" which provides further SNR enhancement and a "shunted input multiplicative coupling mode" which amplifies noise-to-noise couplings and leads to derivation of better readout threshold for diagnostics decision making. Also, a combination of different resonance interactions can be exploited.

Details regarding a related implementation may be found in co-pending U.S. patent application Ser. No. 09/253,792, now U.S. Pat. No. 6,142,681, filed contemporaneously herewith, entitled "Method and Apparatus for Interpreting Hybridized Bioelectronic DNA Microarray Patterns Using Self Scaling Convergent Reverberant Dynamics", and incorporated by reference herein. Details regarding an implementation directed to measuring viral loads may be found in co-pending U.S. patent application Ser. No. 09/253,791, now U.S. Pat. No. 6,235,511, also filed contemporaneously herewith, entitled "Method and Apparatus for Exponentially Convergent Therapy Effectiveness Monitoring Using DNA Microarray Based Viral Load Measurements", and also incorporated by reference herein.

The exemplary embodiments have been primarily described with reference to flow charts illustrating pertinent features of the embodiments. Each method step may also represent a hardware or software component for performing the corresponding step. It should be appreciated that not all components or method steps of a complete implementation of a practical system are necessarily illustrated or described in detail. Rather, only those components or method steps necessary for a thorough understanding of the invention have been illustrated and described in detail. Actual implementations may utilize more steps or components or fewer steps or components.

The description of the exemplary embodiments is provided to enable any person skilled in the art to make or use the present invention. Various modifications to these embodiments will be readily apparent to those skilled in the art and the generic principles defined herein may be applied to other embodiments without the use of the inventive faculty. Thus, the invention is not intended to be limited to the embodiments shown herein but is to be accorded the widest scope consistent with the principles and novel features disclosed herein.

What is claimed is:

1. A method for determining the presence of specific constituents within a biological sample based on an output pattern generated from a detected image of the biological sample applied to an array, wherein the output pattern comprises signals associated with noise, and signals associated with the biological sample which have intensities both greater and less than intensities of signals associated with noise, the method comprising the steps of:

utilizing signal processing to amplify signals associated with the biological sample having an intensity lower than the intensity of signals associated with noise, to an intensity greater than the intensity of the signals associated with noise to generate a modified output pattern;

determining which signals within the modified output pattern correlate with specific constituents within the biological sample; and determining specific constituents within the biological sample based on the signals within the modified output pattern correlating to specific constituents within the biological sample.

2. The method of claim 1 wherein the signal processing utilizes interferometery to amplify the signals associated with the biological sample having an intensity lower than the intensity of signals associated with noise to an intensity greater than the intensity of the signals associated with noise to generate a modified output pattern.

3. The method of claim 2 wherein the utilized interferometry is resonance interferomtery.

4. The method of claim 3 wherein the utilized resonance interferometry is quantum resonance interferometry.

5. The method of claim 3 wherein the utilized resonance interferometry is stochastic resonance interferometry.

6. A method for analyzing output patterns of arrayed information structures to determine the presence of specific constituents within a biological sample applied to the arrayed information structures, wherein the output pattern comprises signals associated with noise, and signals correlating to the biological sample with the signals correlating to the biological sample having intensities both greater and less than the signals associated with noise, the method comprising the steps of:

utilizing interferometry to amplify signals associated with the biological sample having an intensity lower than the intensity of signals associated with noise, to an intensity greater than the intensity of the signals associated with noise to generate a modified output pattern;

determining which signals within the modified output pattern correlate with specific constituents within the biological sample, and determining specific constituents within the biological sample based on the signals within the modified output pattern correlating to specific constituents within the biological sample.

7. The method of claim 6 wherein the utilized interferometry is resonance interferometry.

8. The method of claim 7 wherein the utilized resonance interferometry is quantum resonance interferometry.

9. The method of claim 7 wherein the utilized resonance interferometry is stochastic resonance interferometry.

10. A system for determining the presence of specific constituents within a biological sample based on an output pattern generated from a detected image of the biological sample applied to an array wherein the output pattern comprises signals associated with noise, and signals associated with the biological sample which have intensities both greater and less than intensities of signals associated with noise, comprising:

means for amplifying signals associated with the biological sample having an intensity lower than the intensity of signals associated with noise, to an intensity greater than the intensity of the signals associated with noise to generate a modified output pattern;

means for determining which signals within the modified output pattern correlate with specific constituents within the biological sample; and means for determining specific constituents within the biological sample based on the signals within the modified output pattern correlating to specific constituents within, the biological sample.

11. The system of claim 10 wherein the means for amplifying signals utilizes interferometery to amplify the signals associated with the biological sample having an intensity lower than the intensity of signals associated with noise, to an intensity greater than the intensity of the signals associated with noise to generate a modified output pattern.

12. The system of claim 11 wherein the utilized interferometry is resonance interferomtery.

13. The system of claim 12 wherein the utilized resonance interferometry is quantum resonance interferometry.

14. The system of claim 12 wherein the utilized resonance interferometry is stochastic resonance interferometry.

15. A system for determining the presence of specific constituents within a biological sample based on an output pattern generated from a detected image of the biological sample applied to an array wherein the output pattern comprises signals associated with noise, and signals associated with the biological sample which have intensities both greater and less than intensities of signals associated with noise, comprising:

signal processing means for amplifying signals associated with the biological sample having an intensity lower than the intensity of signals associated with noise, to an intensity greater than the intensity of the signals associated with noise to generate a modified output pattern;

first determination means for determining which signals within the modified output pattern correlate with specific constituents within the biological sample; and second determination mean to determining specific constituents within the biological sample based on the signals within the modified output pattern correlating to specific constituents within the biological sample.

16. A computer code product, embodied on computer-readable media, for determining the presence of specific constituents within a biological sample based on an output pattern generated from a detected image of the biological sample applied to an array, wherein the output pattern comprises signals associated with noise, and signals associated with the biological sample which have intensities both greater and less than intensities of signals associated with noise, comprising:

computer code that utilizes signal processing to amplify signals associated with the biological sample having an intensity lower than the intensity of signals associated with noise, to an intensity greater than the intensity of the signals associated with noise to generate a modified output pattern;

computer cede that determines which signals within the modified output pattern correlate with specific constituents within the biological sample; and computer code that determines specific constituents within the biological sample based on the signals within the modified output pattern correlating to specific constituents within the biological sample.

17. A computer code product, embodied on computer-readable media, for analyzing output patterns of arrayed information structures to determine the presence of specific constituents within a biological sample applied to the arrayed information structures, wherein the output pattern comprises signals associated with noise, and signals correlating to the biological sample with the signals correlating to the biological sample having intensities both greater and less than the signals associated with noise, comprising:

computer code that utilizes interferometry to amplify signals associated with the biological sample having an intensity lower than the intensity of signals associated with noise, to an intensity greater than the intensity of the signals associated with noise to generate a modified output pattern;

computer code that determines which signals within the modified output pattern correlate with specific constituents within the biological sample; and computer code that determines specific constituents within the biological sample based on the signals within the modified output pattern correlating to specific constituents within the biological sample.

18. A method for determining the presence of events of interest within an output pattern generated from a detected image of en array of detectors, wherein the events of interest correspond to at least one signal from a detector and wherein the output pattern comprises signals associated with noise, and signals associated with the events of interest which have intensities both greater and less than intensities of signals associated with noise, the method comprising the steps of:

utilizing quantum resonance interferometry to amplify signals associated with the events of interest having an intensity lower than the intensity of signals associated with noise, to an intensity greater than the intensity of the signals associated with noise to generate a modified output pattern;

determining which signals within the modified output pattern correlate with events of interest; and determining whether specific events of interest have occurred based on the signals within the modified output pattern correlating to the events of interest.

19. A system for determining the presence of events of interest within an output pattern generated from a detected image of an array of detectors, wherein the events of interest correspond to at least one signal from a detector and wherein the output pattern comprises signals associated with noise, and signals associated with the events of interest which have intensities both greater and less than intensities of signals associated with noise, comprising:

quantum resonance interferometry means for amplifying signals associated with the events of interest having an intensity lower than the intensity of signals associated with noise, to an intensity greater than the intensity of the signals associated with noise to generate a modified output pattern:

means for determining which signals within the modified output pattern correlate with events of interest; and means for determining whether specific events of interest have occurred based on the signals within the modified output pattern correlating to the events of interest.

20. A computer code product, embodied on computer-readable media, for determining the presence of events of interest within an output pattern generated from a detected image of an array of detectors, wherein the events of interest correspond to at least one signal from a detector and wherein the output pattern comprises signals associated with noise, and signals associated with the events of interest which have intensities both greater and less than intensities of signals associated with noise, comprising:

computer code that utilizes quantum resonance interferometry to amplify signals associated with the events of interest having an intensity lower than the intensity of signals associated with noise, to an intensity greater than the intensity of the signals associated with noise to generate a modified output pattern;

computer code that determines which signals within the modified output pattern correlate with events of interest; and computer code that determines whether specific events of interest have occurred based on the signals within the modified output pattern correlating to the events of interest.

* * * * *